United States Patent
Xu et al.

(10) Patent No.: US 12,349,937 B2
(45) Date of Patent: Jul. 8, 2025

(54) CONTINUUM INSTRUMENT AND SURGICAL ROBOT

(71) Applicant: BEIJING SURGERII ROBOTICS COMPANY LIMITED, Beijing (CN)

(72) Inventors: Kai Xu, Beijing (CN); Xu Liu, Beijing (CN)

(73) Assignee: BEIJING SURGERII ROBOTICS COMPANY LIMITED, Beijing (CN)

(*) Notice: Subject to any disclaimer, the term of this patent is extended or adjusted under 35 U.S.C. 154(b) by 394 days.

(21) Appl. No.: 18/010,058

(22) PCT Filed: Mar. 16, 2021

(86) PCT No.: PCT/CN2021/080949
§ 371 (c)(1),
(2) Date: Dec. 13, 2022

(87) PCT Pub. No.: WO2022/001188
PCT Pub. Date: Jan. 6, 2022

(65) Prior Publication Data
US 2023/0225757 A1    Jul. 20, 2023

(30) Foreign Application Priority Data

Jun. 30, 2020 (CN) .......... 202010618709.3
Jun. 30, 2020 (CN) .......... 202010618743.0
Jun. 30, 2020 (CN) .......... 202010618748.3

(51) Int. Cl.
*A61B 17/34* (2006.01)
*A61B 34/30* (2016.01)
*A61B 17/29* (2006.01)

(52) U.S. Cl.
CPC .......... *A61B 17/3423* (2013.01); *A61B 34/30* (2016.02); *A61B 2017/2908* (2013.01)

(58) Field of Classification Search
CPC ................ A61B 17/3423; A61B 34/30; A61B 2017/2908; B25J 18/06
See application file for complete search history.

(56) References Cited

U.S. PATENT DOCUMENTS

2009/0283647 A1* 11/2009 Yasunaga ............... A61B 90/50
248/123.2
2012/0253327 A1    10/2012 Malkowski
(Continued)

FOREIGN PATENT DOCUMENTS

CN    103085083 A    5/2013
CN    106175852 A    12/2016
(Continued)

*Primary Examiner* — Richard G Louis
(74) *Attorney, Agent, or Firm* — SZDC Law PC

(57) ABSTRACT

A continuum instrument includes: at least one proximal continuum, at least one distal continuum, and a drive connection part. The proximal continuum comprises a proximal stop disk and a plurality of proximal structural backbones, the plurality of proximal structural backbones being fixedly connected to the proximal stop disk. The distal continuum comprises a distal stop disk and a plurality of distal structural backbones, the plurality of distal structural backbones being fixedly connected to the distal stop disk, and the plurality of distal structural backbones being fixedly connected to or integrally formed with the plurality of proximal structural backbones. The drive connection part is connected to the proximal stop disk, and an input end of the drive connection part is for driving the proximal stop disk to turn so as to drive the distal continuum to bend.

18 Claims, 18 Drawing Sheets

(56) References Cited

U.S. PATENT DOCUMENTS

| | | | |
|---|---|---|---|
| 2015/0352728 A1* | 12/2015 | Wang | B25J 18/06 74/490.04 |
| 2018/0243900 A1 | 8/2018 | Tanaka et al. | |
| 2019/0193260 A1 | 6/2019 | Xu et al. | |
| 2019/0208989 A1 | 7/2019 | Xu et al. | |

FOREIGN PATENT DOCUMENTS

| | | | |
|---|---|---|---|
| CN | 106217345 A | 12/2016 | |
| CN | 106308938 A | 1/2017 | |
| CN | 109431602 A | 3/2019 | |
| CN | 109452976 A | 3/2019 | |
| CN | 111319033 A | 6/2020 | |
| EP | 0312602 A1 | 4/1989 | |
| WO | 2018041206 A1 | 3/2018 | |
| WO | 2020118848 A1 | 6/2020 | |

* cited by examiner

121

121

CONTINUUM INSTRUMENT AND SURGICAL ROBOT

CROSS REFERENCE TO RELATED APPLICATIONS

The present application is the National Stage Application of PCT/CN2021/080949, filed on Mar. 16, 2021, which claims the right of priority of the Chinese patent application No. 2020106187483, filed on Jun. 30, 2020, and entitled "Integrally Drivable Flexible Continuum Structure and Flexible Mechanical Arm", the Chinese patent application No. 2020106187093, filed on Jun. 30, 2020, and entitled "Surgical Tool Drive Transmission System Based on Rotational Drive Mechanism", and the Chinese patent application No. 2020106187430, filed on Jun. 30, 2020, and entitled "Surgical Tool Drive Transmission System Based on Rotary-Linear Drive, and Surgical Robot", which are incorporated herein by reference in their entirety.

TECHNICAL FIELD

The present disclosure relates to the field of medical instruments, and in particular to a continuum instrument and a surgical robot.

BACKGROUND ART

Minimally invasive procedures cause less injury to patients and faster postoperative recovery, and have been of great significance in surgery. In a minimally invasive procedure, surgical instruments, including surgical tools and visual lighting modules, all enter the human body through an incision or a natural orifice and then reach a surgical site to perform a surgical operation. In an existing surgical instrument, a distal structure is mainly composed of multiple rods hinged in series, and is driven by a pulling force from a steel wire rope so that the surgical instrument can bend at a hinged joint. Since the steel wire rope must be maintained in a continuous tension state by means of a pulley, this driving method can hardly achieve further miniaturization of the surgical instrument and further improvement of kinematic performance of the instrument.

In contrast to a traditional rigid kinematic chain which achieves a bending motion by means of mutual rotation at joints, a flexible continuum structure can achieve continuous bending deformation, and thus the flexible continuum structure is widely used in the research and development of medical instruments such as flexible manipulators, endoscopes and controllable catheters, and new-type special equipment such as industrial deep-cavity detection endoscopes and flexible mechanical arms.

Generally, in an existing continuum structure, a drive wire in the continuum structure is directly pushed and pulled by means of a drive mechanism so that the continuum structure can bend in any direction. However, with the stricter requirements for a continuum structure, such as high precision, fast response, high flexibility of bending, and good stability, the existing drive structures gradually no longer satisfy the above requirements. In addition, in the existing driving method, the motion is performed by means of directly pushing and pulling a drive wire, and thus when there is a large number of drive wires, the number of drive mechanisms will also increase accordingly, making the structure complex.

SUMMARY OF THE INVENTION

In some embodiments, the present disclosure provides a continuum instrument, comprising: at least one proximal continuum comprising a proximal stop disk and a plurality of proximal structural backbones, with proximal ends of the plurality of proximal structural backbones being fixedly connected to the proximal stop disk; at least one distal continuum comprising a distal stop disk and a plurality of distal structural backbones, with distal ends of the plurality of distal structural backbones being fixedly connected to the distal stop disk, and the plurality of distal structural backbones being fixedly connected to or integrally formed with the plurality of proximal structural backbones; and a drive connection part connected to the proximal stop disk, the drive connection part comprising an input end located at a proximal side of the proximal stop disk, the input end is for driving the proximal stop disk to turn so as to drive the distal continuum to bend by means of the proximal structural backbones and the distal structural backbones.

In some embodiments, the present disclosure provides a surgical robot, comprising at least one surgical trolley, at least one positioning arm, and at least one surgical instrument, wherein the at least one surgical instrument comprises at least one continuum instrument as described above and an end device disposed at a distal end of the continuum instrument; and the at least one positioning arm is movably disposed on the at least one surgical trolley, and at least one surgical instrument is disposed at a distal end of the at least one positioning arm.

BRIEF DESCRIPTION OF THE DRAWINGS

In order to explain the technical solutions in the embodiments of the present disclosure more clearly, the accompanying drawings used in the description of the embodiments will be briefly introduced below. Obviously, the accompanying drawings in the following description only show some of the embodiments of the present disclosure, and for those of ordinary skill in the art, other embodiments would also have been obtained from the contents of the embodiments of the present disclosure and these accompanying drawings without involving any inventive effort.

DETAILED DESCRIPTION OF THE EMBODIMENTS

In order to clarify the technical problem to be solved, the technical solutions used and the technical effects achieved in the present disclosure in a better way, the technical solutions of embodiments of the present disclosure will be described in further detail below in conjunction with the accompanying drawings. Obviously, the embodiments described are merely exemplary embodiments, rather than all the embodiments of the present disclosure.

In the description of the present disclosure, it should be noted that the orientation or position relationships indicated by the terms "center", "upper", "lower", "left", "right", "vertical", "horizontal", "inner", "outer", etc. are based on the orientation or position relationships shown in the accompanying drawings and are merely for ease of description of the present disclosure and simplification of the description, rather than indicating or implying that the devices or elements referred to must have a specific orientation or be constructed and operated in a specific orientation, and thus cannot be construed as limiting the present disclosure. Moreover, the terms "first" and "second" are merely used for the illustrative purpose, and should not be construed as indicating or implying the relative importance. In the description of the present disclosure, it should be noted that the terms "mounting", "connecting", "connection" and "coupling" should be appreciated in a generalized sense, unless otherwise explicitly specified and defined, and for example, may be a fixed connection or a detachable connection, may be a mechanical connection or an electrical connection, may be a direct connection or an indirect connection via an intermediate medium, and may be communication between the interiors of two components. For those of ordinary skill in the art, the specific meanings of the terms mentioned above in the present disclosure should be construed according to specific circumstances. The present disclosure defines the end close to an operator (e.g., a surgeon) as a proximal end or portion or a rear end or portion, and the end close to a patient undergoing surgery as a distal end or portion or a front end or portion. Those skilled in the art will appreciate that the embodiments of the present disclosure can be used in medical instruments or surgical robots, and can also be used in other non-medical devices.

Figure 1:
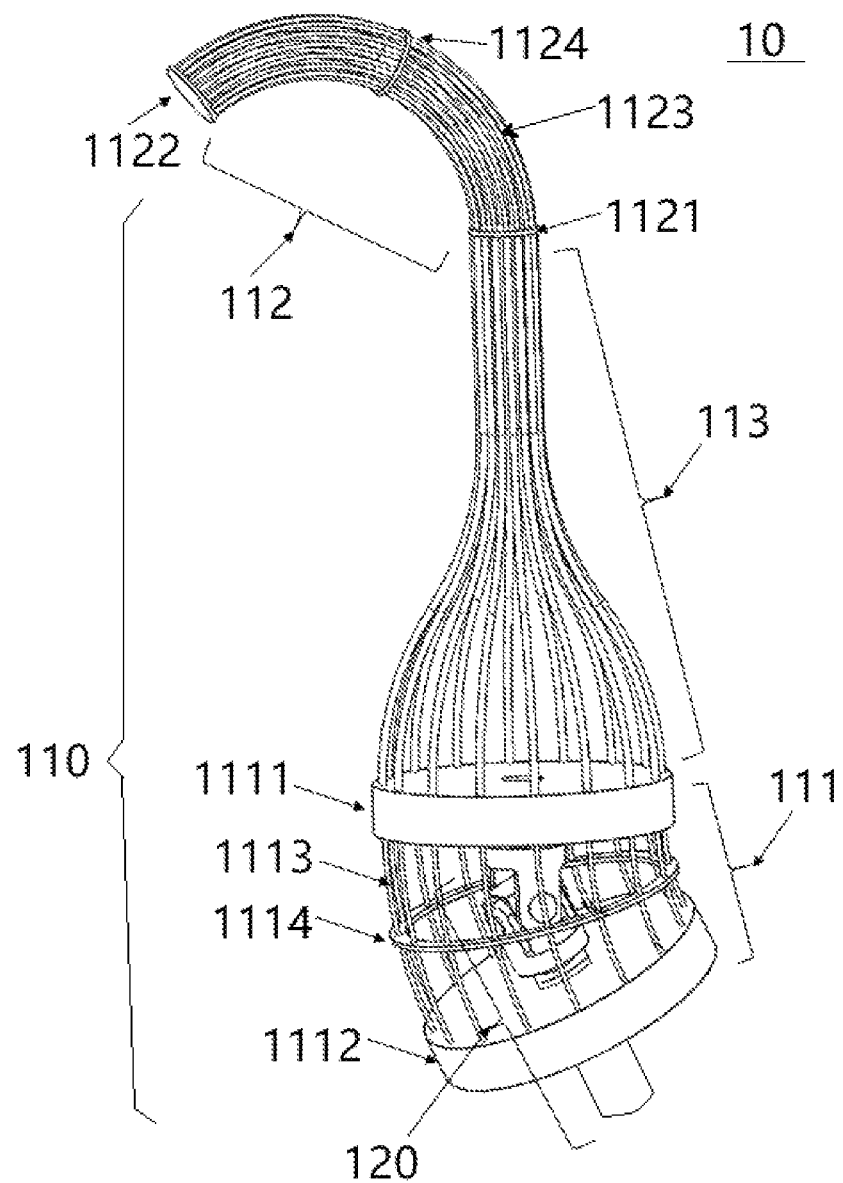
FIG. 1 shows a schematic structural diagram of a continuum instrument according to some embodiments of the present disclosure.

FIG. 1 shows a continuum instrument 10 according to some embodiments of the present disclosure. As shown in FIG. 1, the continuum instrument 10 may include a flexible continuum structure 110 and a drive connection part 120. The flexible continuum structure 110 may include at least one proximal continuum 111 located at a proximal end, and at least one distal continuum 112 located at a distal end. The proximal continuum 111 may include a proximal base disk 1111, a proximal stop disk 1112, and proximal structural backbones 1113. The proximal base disk 1111 and the proximal stop disk 1112 are arranged at an interval. Proximal ends of the plurality of proximal structural backbones 1113 are fixedly connected to the proximal stop disk 1112, and distal ends of the plurality of proximal structural backbones 1113 pass through the proximal base disk 1111. The distal continuum 112 may include a distal base disk 1121, a distal stop disk 1122, and distal structural backbones 1123. The distal base disk 1121 and the distal stop disk 1122 are arranged at an interval, and the distal base disk 1121 is adjacent to the proximal base disk 1111. Distal ends of the plurality of distal structural backbones 1123 are fixedly connected to the distal stop disk 1122, and proximal ends of the plurality of distal structural backbones 1123 pass through the distal base disk 1121 and are then fixedly connected to or integrally formed with the plurality of proximal structural backbones 1113. The drive connection part 120 is connected to the proximal stop disk 1112. The drive connection part 120 comprises an input end located at the proximal side of the proximal stop disk 1112, and the input end is for being driven by the drive transmission mechanism to bring the proximal stop disk 1112 to move and turn so as to push and pull the proximal structural backbones 1113, so that the distal continuum 112 bends in a space in different directions. In some embodiments, a distal end of the drive connection part 120 is connected to the proximal base disk 1111, and a proximal end of the drive connection part 120 passes through the proximal stop disk 1112 and is connected to the proximal stop disk 1112, as shown in FIG. 1.

Figure 2A:
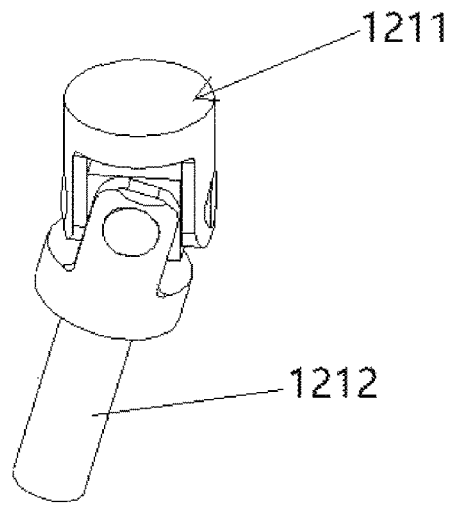
FIG. 2(a) shows a schematic structural diagram of a universal coupling joint of a drive connection part according to some embodiments of the present disclosure.
Figure 2B:
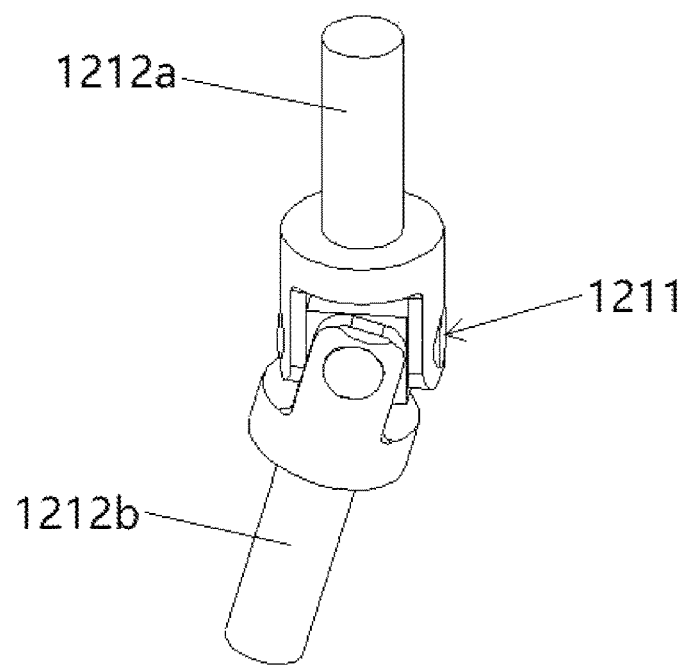
FIG. 2(b) shows a schematic structural diagram of another universal coupling joint of a drive connection part according to some embodiments of the present disclosure.

In some embodiments, the drive connection part 120 may include at least one joint, such as a universal coupling joint, a spherical hinge joint, or a hinge joint. FIG. 2(a) shows a schematic structural diagram of a universal coupling joint 121 of the drive connection part 120 according to some embodiments of the present disclosure, and FIG. 2(b) shows a schematic structural diagram of another universal coupling joint 121 according to some embodiments of the present disclosure. In some embodiments, as shown in FIG. 2(a), the drive connection part 120 may include the universal coupling joint 121. The universal coupling joint 121 may include one universal coupling 1211 or multiple universal couplings 1211 (e.g., multiple universal couplings connected in series), and the one or multiple universal couplings 1211 are located between the proximal base disk 1111 and the proximal stop disk 1112. The universal coupling 1211 may include two rotating pairs which have axes of rotation intersecting each other, with the axis of rotation of one of the rotating pairs being disposed in a radial direction. It should be appreciated that the radial direction may be perpendicular to an axial direction of the drive connection part 120 located at an initial position, with the initial position referring to a natural extended state of the drive connection part 120 when not be driven. In some embodiments, as shown in FIG. 2(*a*), the universal coupling joint 121 may include at least one universal coupling 1211 and at least one link rod 1212. In some embodiments, the drive connection part 120 may include the universal coupling 1211 located at a distal end and the link rod 1212 located at a proximal end. A distal end of the link rod 1212 is connected to the universal coupling 1211, and a distal end of the universal coupling 1211 (the distal end of the drive connection part 120) is connected to the proximal base disk 1111. A proximal end of the link rod 1212 (the proximal end of the drive connection part 120) passes through the proximal stop disk 1112 and is connected to the proximal stop disk 1112. In some embodiments, as shown in FIG. 2(*b*), the drive connection part 120 may include link rods 1212*a-b* and the universal coupling 1211 located between the link rods 1212*a-b*, and the link rods 1212*a-b* (the proximal end and the distal end of the drive connection part 120) are separately connected to the proximal base disk 1111 and the proximal stop disk 1112.

As shown in FIG. 1, in some embodiments, the flexible continuum structure 110 may further include a structural backbone guide tube bundle 113. A proximal end of the structural backbone guide tube bundle 113 is fixedly connected to the proximal base disk 1111, and a distal end of the structural backbone guide tube bundle 113 is fixedly connected to the distal base disk 1121. The distal ends of the plurality of proximal structural backbones 1113 sequentially pass through the proximal base disk 1111, and the structural backbone guide tube bundle 113 is separately connected to the plurality of distal structural backbones 1123. The structural backbone guide tube bundle 113 may guide and constrain a plurality of proximal structural backbones 1113 located between the proximal base disk 1111 and the distal base disk 1121.

Figure 3:
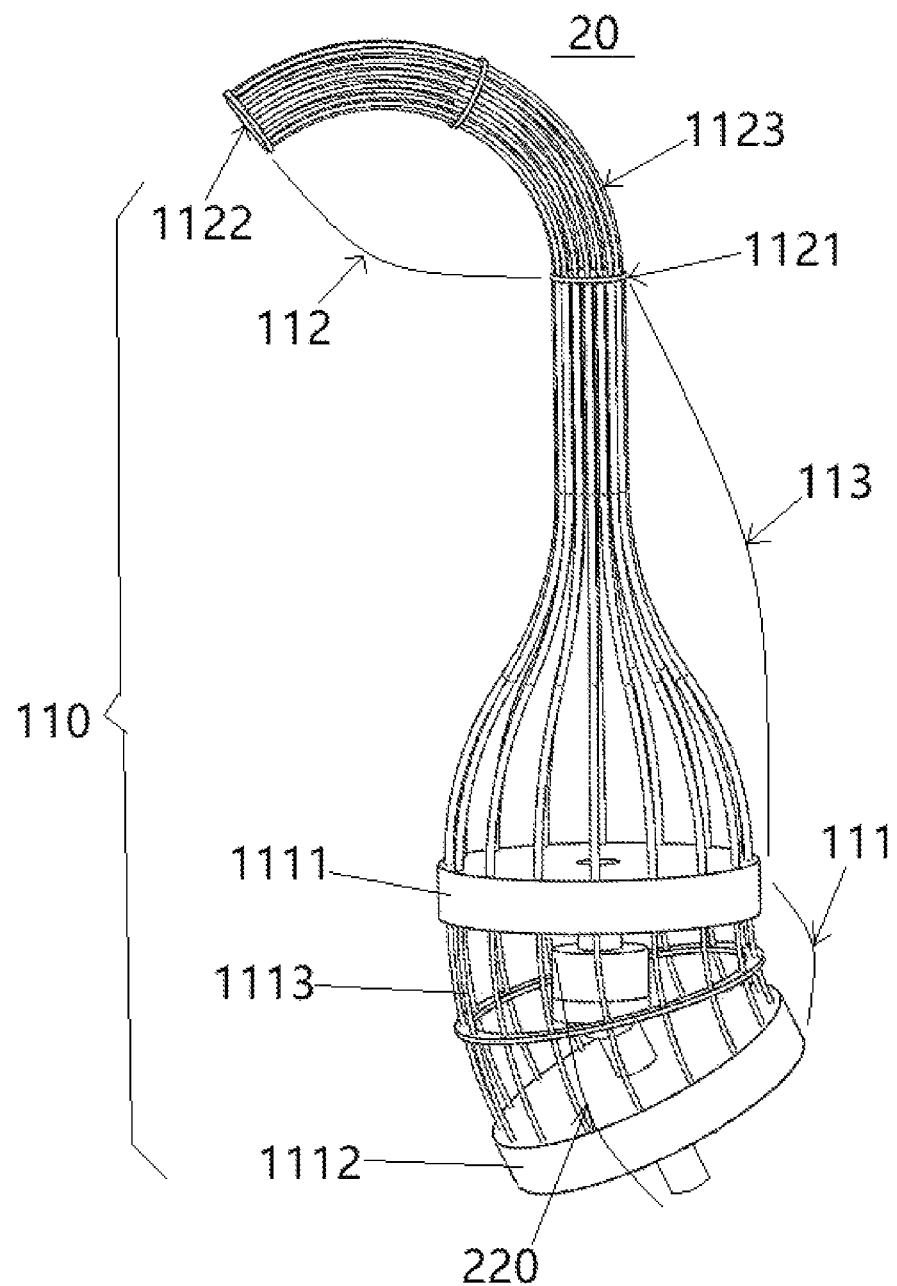
FIG. 3 shows a schematic structural diagram of another continuum instrument according to some embodiments of the present disclosure.

FIG. 3 shows a continuum instrument 20 according to some embodiments of the present disclosure. As shown in FIG. 3, the continuum instrument 20 may include a flexible continuum structure 110 and a drive connection part 220. FIG. 4(*a*) shows a schematic structural diagram of a spherical hinge joint 221 of the drive connection part 220 according to some embodiments of the present disclosure, and FIG. 4(*b*) shows a schematic structural diagram of another spherical hinge joint 221 according to some embodiments of the present disclosure. In some embodiments, as shown in FIG. 4(*a*), the drive connection part 220 may include the spherical hinge joint 221. The spherical hinge joint 221 may include one spherical hinge 2211 or multiple spherical hinges 2211 (e.g., multiple spherical hinges 2211 connected in series). At least one spherical hinge 2211 is located between the proximal base disk 1111 and the proximal stop disk 1112. The spherical hinge 2211 may include three rotating pairs which have axes intersecting each other. In some embodiments, the spherical hinge joint 221 of FIG. 4(*a*) may include at least one spherical hinge 2211 and at least one link rod 2212. In some embodiments, the drive connection part 220 may include the spherical hinge 2211 located at the distal end and the link rod 2212 located at the proximal end. A distal end of the link rod 2212 is connected to the spherical hinge 2211, a distal end of the spherical hinge 2211 (the distal end of the drive connection part 220) is connected to the proximal base disk 1111, and a proximal end of the link rod 2212 (the proximal end of the drive connection part 220) passes through the proximal stop disk 1112 and is connected to the proximal stop disk 1112. In some embodiments, the drive connection part 220 of FIG. 4(*b*) may include link rods 2212*a-b* and the spherical hinge 2211 located between the link rods 2212*a-b*, and the link rods 2212*a-b* (the proximal end and the distal end of the drive connection part 220) are separately connected to the proximal base disk 1111 and the proximal stop disk 1112.

Figure 5:
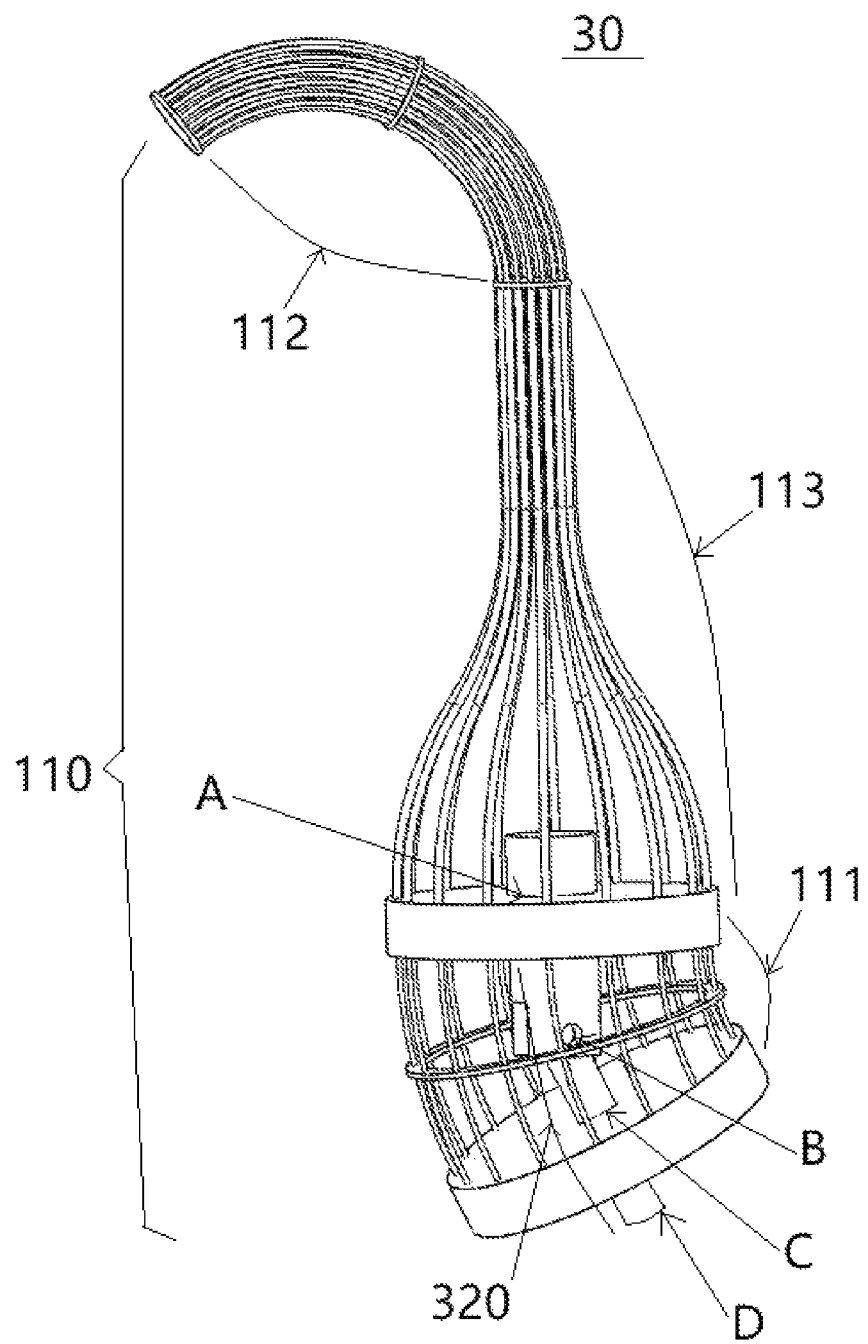
FIG. 5 shows a schematic structural diagram of another continuum instrument according to some embodiments of the present disclosure.
Figure 6:
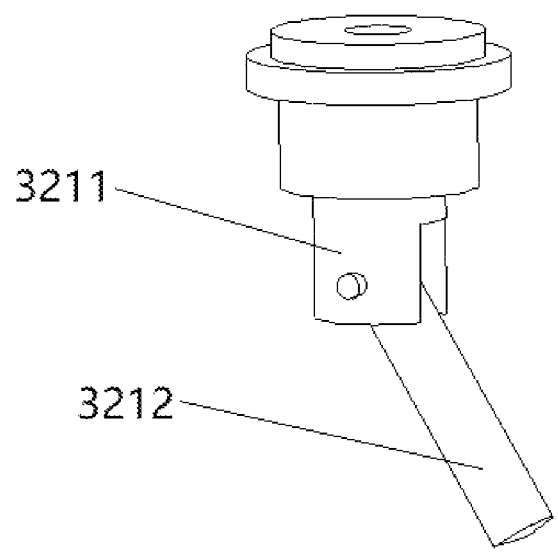
FIG. 6 shows a schematic structural diagram of a hinge joint of a drive connection part according to some embodiments of the present disclosure.

FIG. 5 shows a continuum instrument 30 according to some embodiments of the present disclosure. As shown in FIG. 5, the continuum instrument 30 may include a flexible continuum structure 110 and a drive connection part 320. FIG. 6 shows a schematic structural diagram of a hinge joint 321 of the drive connection part 320 according to some embodiments of the present disclosure. As shown in FIG. 6, in some embodiments, the drive connection part 320 may include the hinge joint 321. The hinge joint 321 may include at least one distal link rod 3211 and at least one proximal link rod 3212 hinged to each other. In some embodiments, the distal link rod 3211 is rotatably connected to the proximal base disk 1111 in an axial direction of the distal link rod 3211, and the proximal link rod 3212 is rotatably connected to the proximal stop disk 1112 in an axial direction of the proximal link rod 3212. The hinge axis about which the distal link rod 3211 and the proximal link rod 3212 are hinged to each other is perpendicular to the axial directions of the distal link rod 3211 and the proximal link rod 3212. A proximal end of the proximal link rod 3212 penetrates the proximal stop disk 1112, and the portion of the proximal link rod 3212 that is located at the proximal side of the proximal stop disk 1112 forms an input end of the drive connection part 320.

Figure 7:
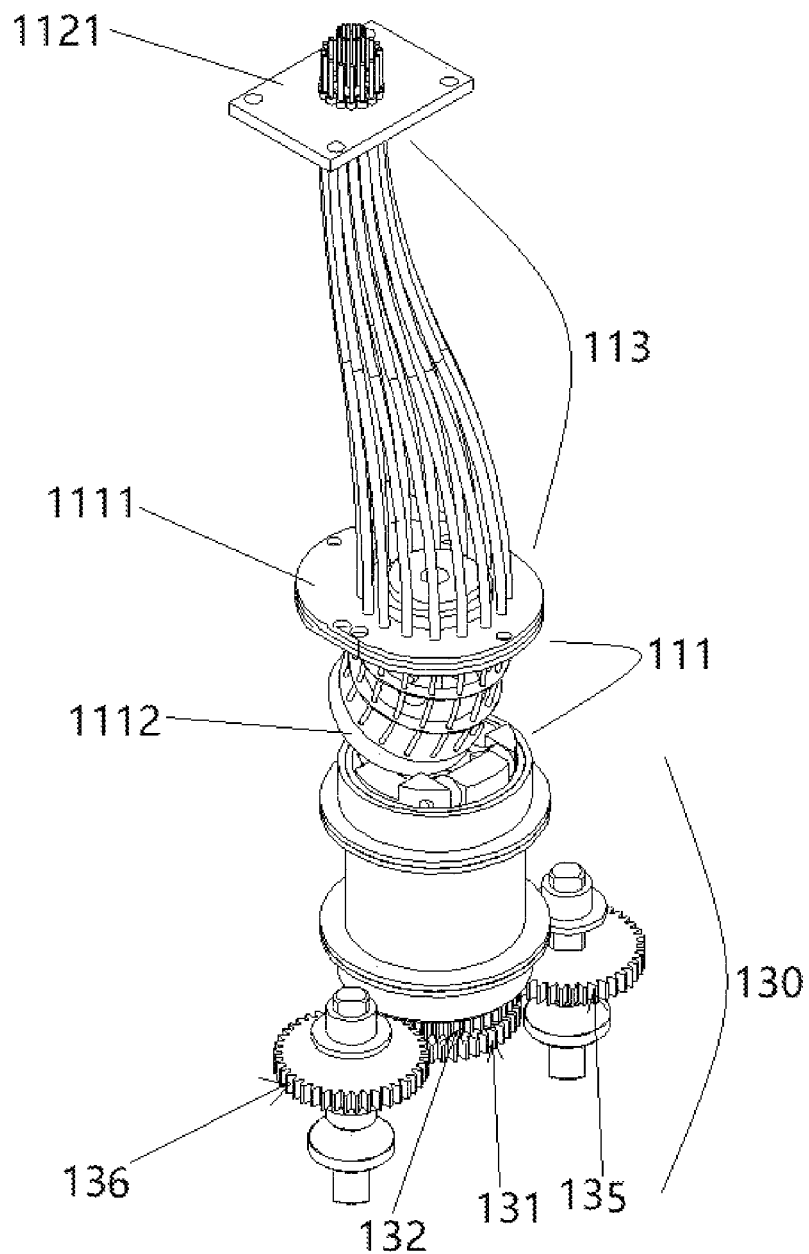
FIG. 7 shows a partial schematic structural diagram of another continuum instrument according to some embodiments of the present disclosure.
Figure 8:
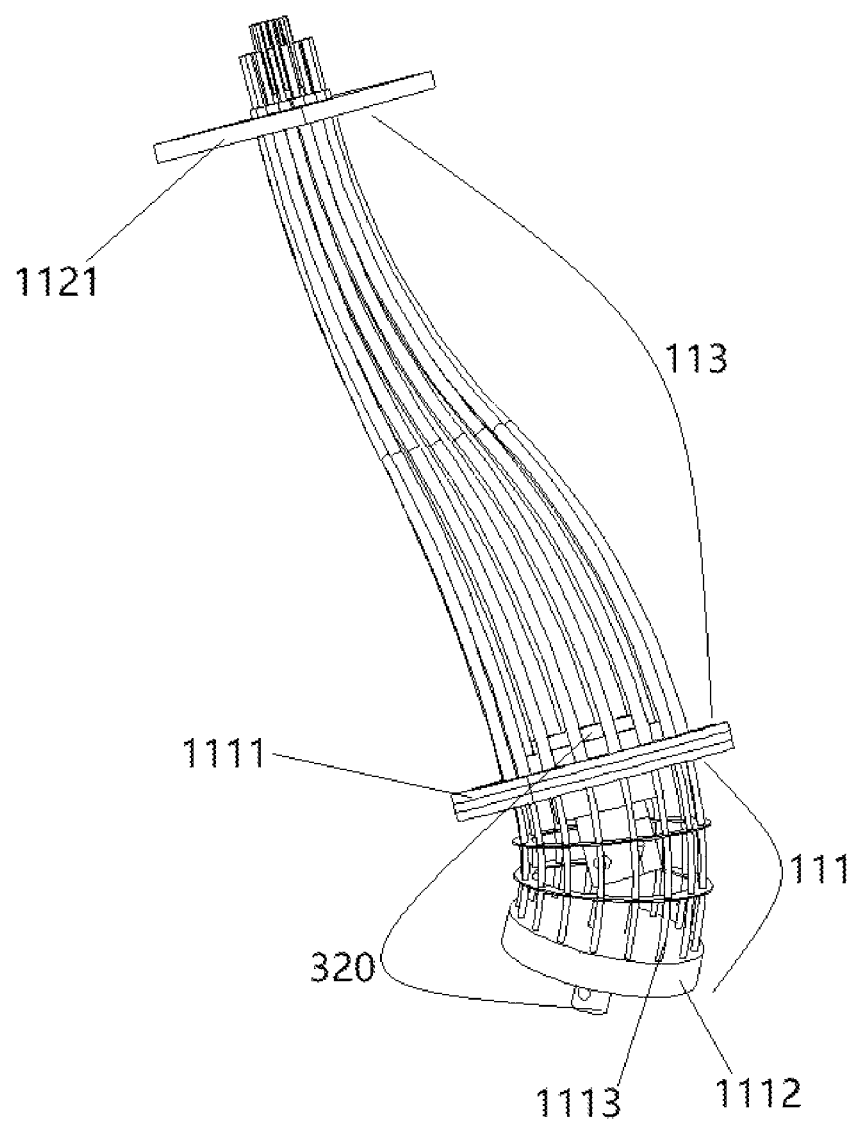
FIG. 8 shows a partial schematic structural diagram of the continuum instrument shown in FIG. 7 according to some embodiments of the present disclosure.
Figure 9:
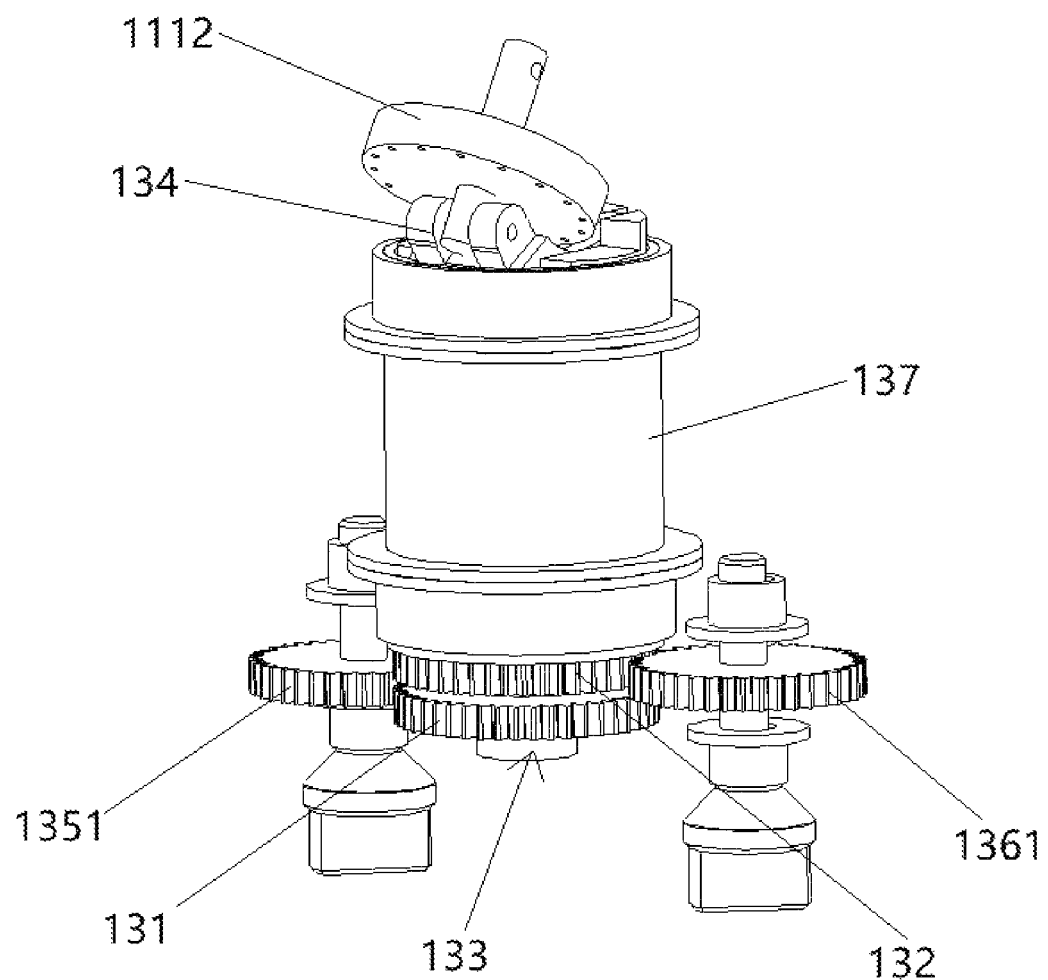
FIG. 9 shows a schematic structural diagram of a drive transmission mechanism according to some embodiments of the present disclosure.

In some embodiments, the continuum instrument 10 (or 20, 30) may further include a drive transmission mechanism. An output end of the drive transmission mechanism may perform a non-planar motion. FIGS. 7 and 8 respectively show a partial schematic structural diagram of a continuum instrument 10 (or 20, 30) according to some embodiments of the present disclosure including a drive transmission mechanism 130. FIG. 9 shows a schematic structural diagram of the drive transmission mechanism 130 according to some embodiments of the present disclosure. In some embodiments, as shown in FIGS. 7-9, the drive transmission mechanism 130 may include a first rotatable member 131, a second rotatable member 132, a rotary-linear motion mechanism 133, and a connecting member 134. The first rotatable member 131 is for being driven by a first drive member 135 to rotate, and the second rotatable member 132 is coaxially disposed with the first rotatable member 131 and is for being driven by a second drive member 136 to rotate relative to the first rotatable member 131. The rotary-linear motion mechanism 133 is connected to the first rotatable member 131 and is for converting a rotational motion of the first rotatable member 131 into a linear motion to be output. One end of the connecting member 134 is hinged to an output end of the rotary-linear motion mechanism 133, and the other end of the connecting member 134 is hinged to the input end of the drive connection part 120 (or 220, 320).

In some embodiments, as shown in FIG. 9, the second rotatable member 132 may be arranged above the first rotatable member 131 in an overlapping manner, and the two rotatable members are rotatable relative to each other. FIG.

Figure 10:
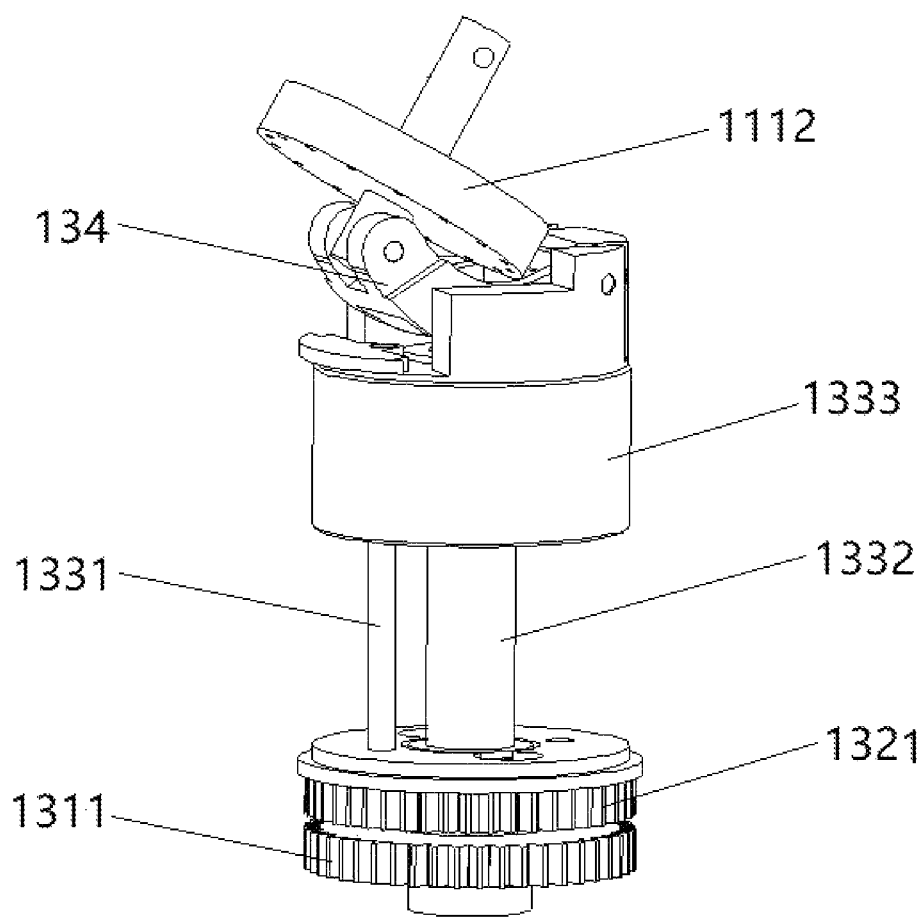
FIG. 10 shows a partial schematic structural diagram of a drive transmission mechanism according to some embodiments of the present disclosure.

10 shows a partial schematic structural diagram of the drive transmission mechanism 130 according to some embodiments of the present disclosure. As shown in FIGS. 9 and 10, in some embodiments, the first rotatable member 131 may include, for example, a first driven gear 1311, the first drive member 135 may include a first driving gear 1351, the second rotatable member 132 may include, for example, a second driven gear 1321, and the second drive member 136 may include a second driving gear 1361. The first driving gear 1351 meshes with the first driven gear 1311, the second driving gear 1361 meshes with the first driven gear 1311, and the second driven gear 1321 is arranged above the first driven gear 1311 in an overlapping manner. The first driving gear 1351 may be driven by a drive electric motor to drive the first driven gear 1311 to rotate, the second driving gear 1361 may be driven by the drive electric motor to drive the second driven gear 1321 to rotate, and the first driven gear 1311 and the second driven gear 1321 are rotatable relative to each other. In some embodiments, the first rotatable member 131 and the second rotatable member 132 may respectively include a first gear and a second gear, the first drive member 135 and the second drive member 136 may include a drive electric motor (or a motor), and the first gear and the second gear can be respectively driven by the drive electric motor to rotate relative to each other. In some embodiments, the transmission mode of the first rotatable member 131 and the second rotatable member 132 may also be other transmission modes, such as belt pulley transmission or sprocket transmission.

Figure 11:
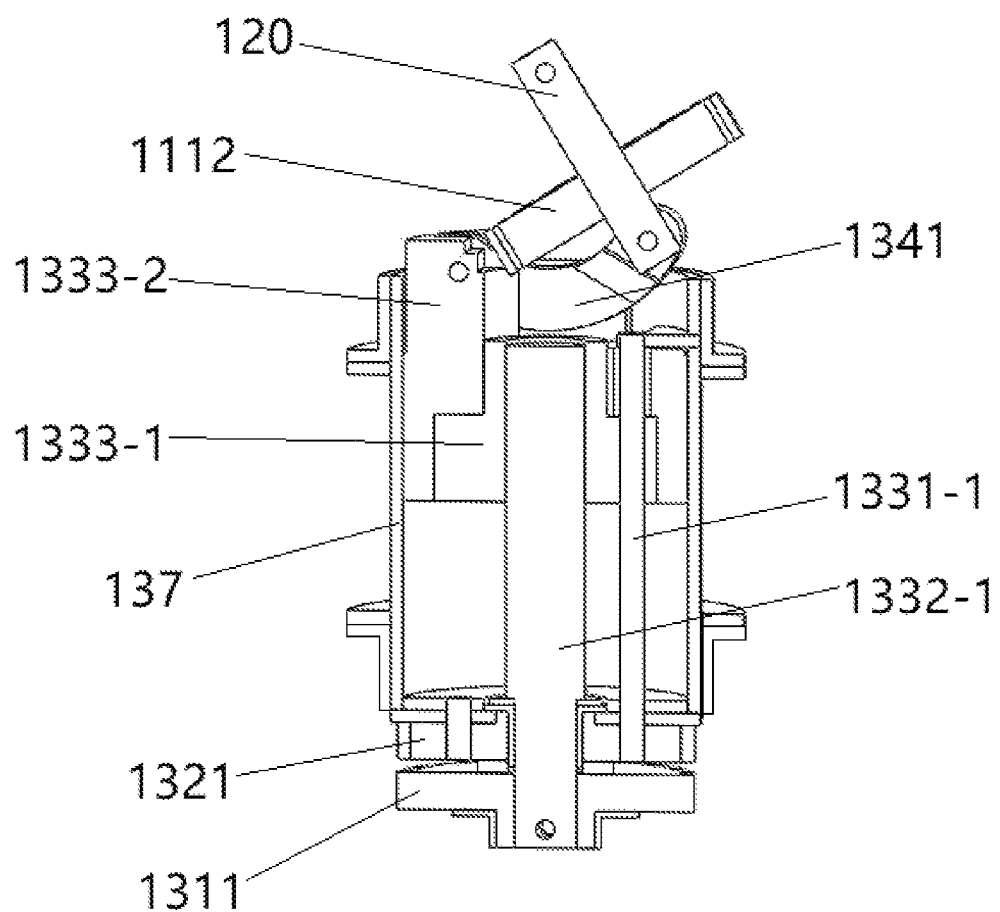
FIG. 11 shows a longitudinal cross-sectional schematic structural diagram of the drive transmission mechanism shown in FIG. 10 according to some embodiments of the present disclosure.

In some embodiments, as shown in FIG. 10, the rotary-linear motion mechanism 133 may include a guide member 1331, a rotary member 1332, and a moving member 1333. A proximal end of the guide member 1331 is fixedly connected to the second rotatable member 132, a proximal end of the rotary member 1332 passes through the second rotatable member 132 and is fixedly connected to the first rotatable member 131, the moving member 1333 is rotatably connected to the rotary member 1332, and the moving member 1333 is for being guided by the guide member 1331 to move linearly in an axial direction of the guide member 1331. FIG. 11 shows a longitudinal cross-sectional schematic structural diagram of the drive transmission mechanism 130 according to some embodiments of the present disclosure. As shown in FIG. 11, in some embodiments, the rotary-linear motion mechanism 133 may include a lead screw and nut structure. As shown in FIG. 11, the guide member 1331 may include a guiding rod 1331-1, the rotary member 1332 may include a lead screw 1332-1, the moving member 1333 includes a nut 1333-1 and a sliding block 1333-2, the nut 1333-1 is rotatably connected to the lead screw 1332-1, and the guiding rod 1331-1 is slidably disposed on the sliding block 1333-2 in a penetrating manner. In some embodiments, the rotary-linear motion mechanism 133 may also be implemented by means of other known structures in the art, such as a ball screw mechanism.

As shown in FIG. 11, in some embodiments, the connecting member 134 may include an arc-shaped link rod 1341. As shown in FIG. 11, in some embodiments, the sliding block 1333-2 may include an upper-layer hinge portion and a lower-layer cylindrical portion which are fixedly connected to each other or integrally formed with each other, the upper-layer hinge portion is for being hinged to one end of the arc-shaped link rod 1341, and the lower-layer cylindrical portion is fixedly sleeved outside the nut 1333-1. For example, the shape of the lower-layer cylindrical portion may match the shape of the nut 1333-1 so as to be adaptively sleeved outside the nut 1333-1.

As shown in FIGS. 9 and 11, in some embodiments, the drive transmission mechanism 130 may further include a barrel-shaped member 137 sleeved outside the moving member 1333, with a proximal end of the barrel-shaped member 137 being fixedly connected to the second rotatable member 132. In some embodiments, the proximal end of the guide member 1331 is fixedly connected to the second rotatable member 132, the distal end of the guide member 1331 is fixedly connected to the barrel-shaped member 137, and the moving member 1333 is slidably disposed on the guide member 1331 in a penetrating manner. As shown in FIG. 11, in some embodiments, the proximal end of the lead screw 1332-1 passes through the second driven gear 1321 and is then coaxially and fixedly connected to the first driven gear 1311. The nut 1333-1 is rotatably connected to the lead screw 1332-1, and the lower-layer cylindrical portion of the sliding block 1333-2 is fixedly connected to the nut 1333-1. The barrel-shaped member 137 is sleeved outside the sliding block 1333-2, and the proximal end of the barrel-shaped member 137 is fixedly connected to the second driven gear 1321. The proximal end of the guiding rod 1331-1 is fixedly connected to the second driven gear 1321, the distal end of the guiding rod 1331-1 is fixedly connected to the distal end of the barrel-shaped member 137, and the lower-layer cylindrical portion of the nut 1333-1 or the sliding block 1333-2 is slidably disposed on the guiding rod 1331-1 in a penetrating manner. One end of the arc-shaped link rod 1341 is hinged to the upper-layer hinge portion of the sliding block 1333-2, and the other end of the arc-shaped link rod 1341 is hinged to the input end of the drive connection part 120 (or 220, 320). The rotary-linear motion mechanism 133 may convert the rotational motion of the first rotatable member 131 into a linear motion to be output.

In some embodiments, the guide member 1331 may include a guide rod and a guide groove (not shown) cooperating with each other, the guide groove may be fixedly disposed on the barrel-shaped member 137 in an axial direction of the barrel-shaped member 137, the guide rod may be slidably disposed in the guide groove in the axial direction of the barrel-shaped member 137, and the guide rod is fixedly connected to the sliding block 1333-2. The rotary-linear motion mechanism 133 may also convert the rotational motion of the first rotatable member 131 into the linear motion to be output.

Thus, as shown in FIGS. 7, 8 and 11, when the first driving gear 1351 drives the first driven gear 1311 located at the lower layer to rotate while the second driving gear 1361 located at the upper layer remains stationary, the lead screw 1332-1 fixed to the first driven gear 1311 rotates correspondingly. The sliding block 1333-2 and the nut 1333-1 cannot rotate due to a limiting effect of the guide member 1331, so that the nut 1333-1 and the sliding block 1333-2 are driven to move up and down in the barrel-shaped member 137, and the arc-shaped link rod 1341 is driven to move, and then the input end of the drive connection part 320 (or 220, 120) is driven to move by means of the arc-shaped link rod 1341. Since the proximal stop disk 1112 can be driven by the drive connection part 320 to turn, the proximal base disk 1111 and the proximal stop disk 1112 are out of alignment and have axes no longer coincident. The proximal stop disk 1112 turns so as to push and pull a plurality of proximal structural backbones 1113 which have ends fixed to the proximal stop disk 1112, so that the plurality of proximal structural backbones 1113 fixed to (e.g., uniformly distributed on) the proximal stop disk 1112 are pulled on one side to increase the corresponding lengths of the proximal structural backbones 1113 in the proximal continuum 111 and are pushed on the other side to decrease the corresponding lengths of the proximal structural backbones 1113 in the proximal continuum 111. However, since the overall length of the proximal structural backbones 1113 is substantially unchanged, resulting in a corresponding change in the length of the distal structural backbones 1123 in the distal continuum 112, the distal continuum 112 is thus driven to bend corresponding to (e.g., in the same direction, in an opposite direction, or angled with) the proximal continuum 111, and the degree of bending of the proximal continuum 111 is then adjusted by means of adjusting the angle of the arc-shaped link rod 1341. In the case where the second driving gear 1361 drives the second driven gear 1321 to rotate, the first driving gear 1351 drives the first driven gear 1311 to rotate, and the second driven gear 1321 and the first driven gear 1311 synchronously rotate in the same direction (e.g., at a constant speed), the vertical position of the sliding block 1333-2 in the barrel-shaped member 137 will not change, but the azimuth angle of the plane of rotation of the arc-shaped link rod 1341 changes. After the proximal continuum 111 is bent, the push and pull action generated on the proximal structural backbones 1113 is transferred to the distal structural backbones 1123 and the distal continuum 112 by means of the structural backbone guide tube bundle 113, so as to achieve the bending of the distal continuum 112 in a space in different directions. The second driven gear 1321 and the first driven gear 1311 are driven cooperatively so as to adjust the degree of bending of the proximal continuum 111 and the bending in different planes. It should be noted that the proportions of bending of the proximal continuum 111 and the distal continuum 112 are respectively inversely proportional to the corresponding distribution radii of the proximal structural backbones 1113 and the distal structural backbones 1123 in the two continua (in this embodiment, the proximal structural backbones 1113 in the proximal continuum 111 and the distal structural backbones 1123 in the distal continuum 112 are respectively distributed in a circumferential direction, may be distributed on a circumference or in a peripheral direction of a rectangular, polygonal, elliptical or other shape, and may be in a uniform or non-uniform distribution, which will not be limited herein). Therefore, when in use, the distribution radii of the proximal structural backbones 1113 and the distal structural backbones 1123 in the proximal continuum 111 and the distal continuum 112 may be respectively adjusted to meet the actual requirements of the proportion of bending.

Figure 12:
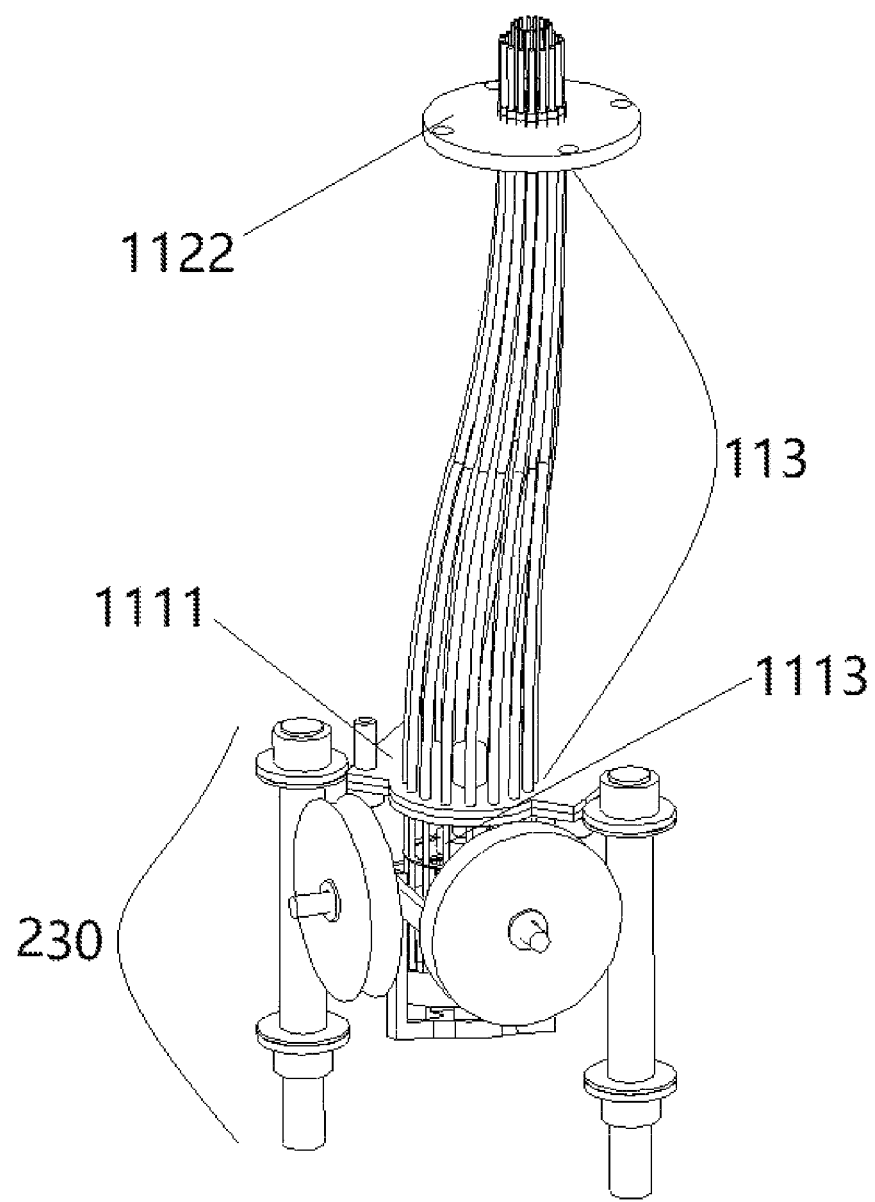
FIG. 12 shows a partial schematic structural diagram of another continuum instrument according to some embodiments of the present disclosure.
Figure 13:
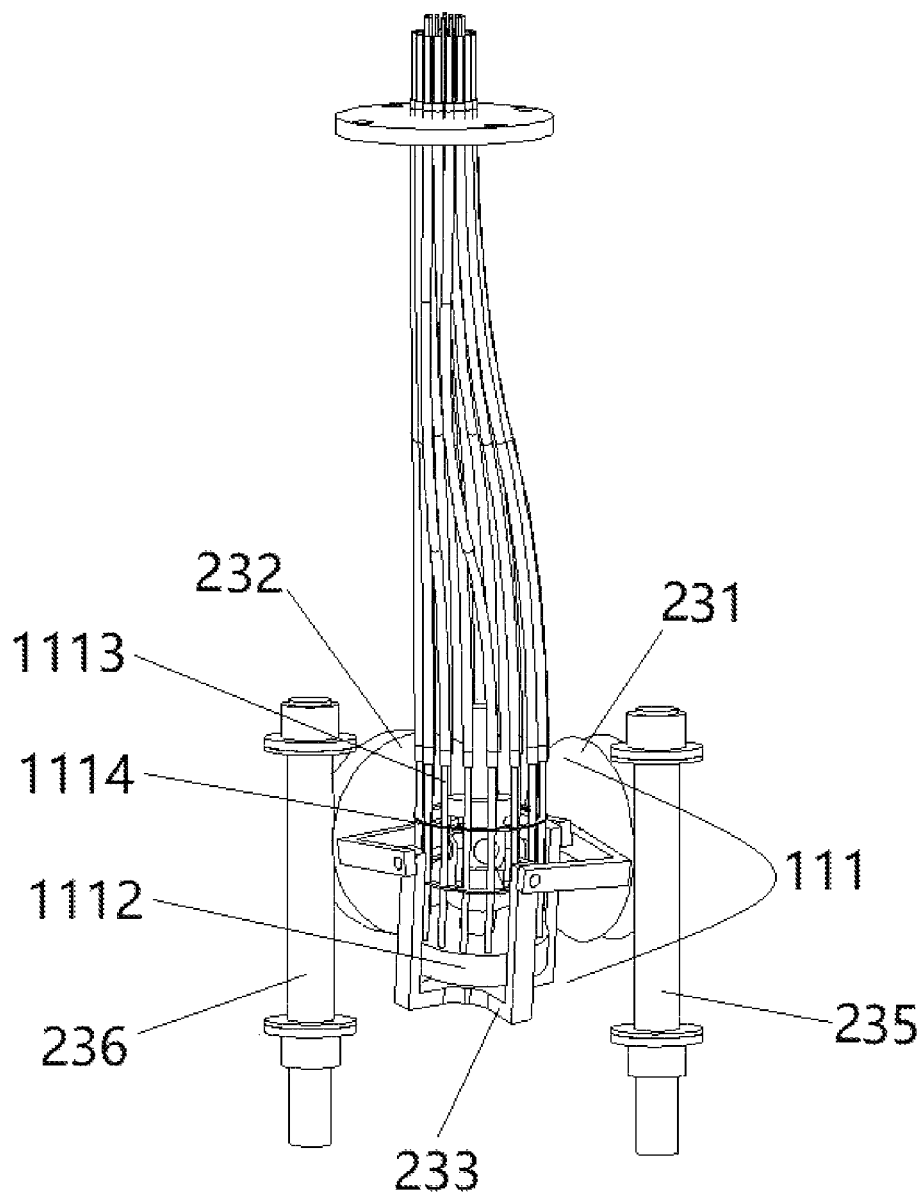
FIG. 13 shows a partial schematic structural diagram of the continuum instrument shown in FIG. 12 according to some embodiments of the present disclosure.
Figure 14:
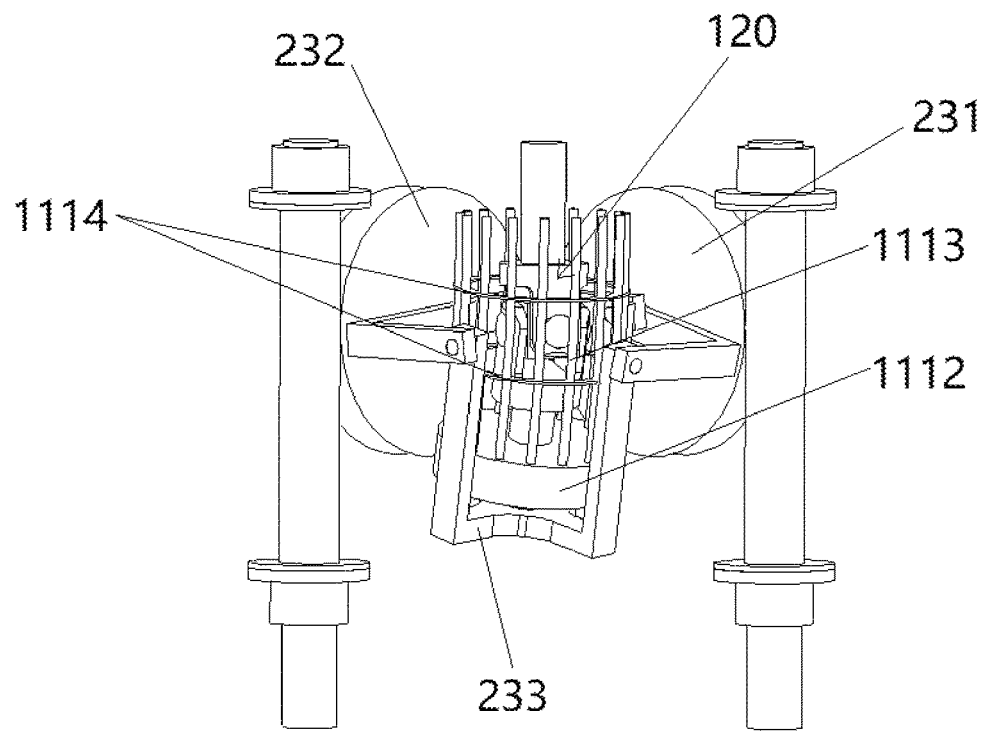
FIG. 14 shows a schematic structural diagram of another drive transmission mechanism according to some embodiments of the present disclosure.
Figure 15:
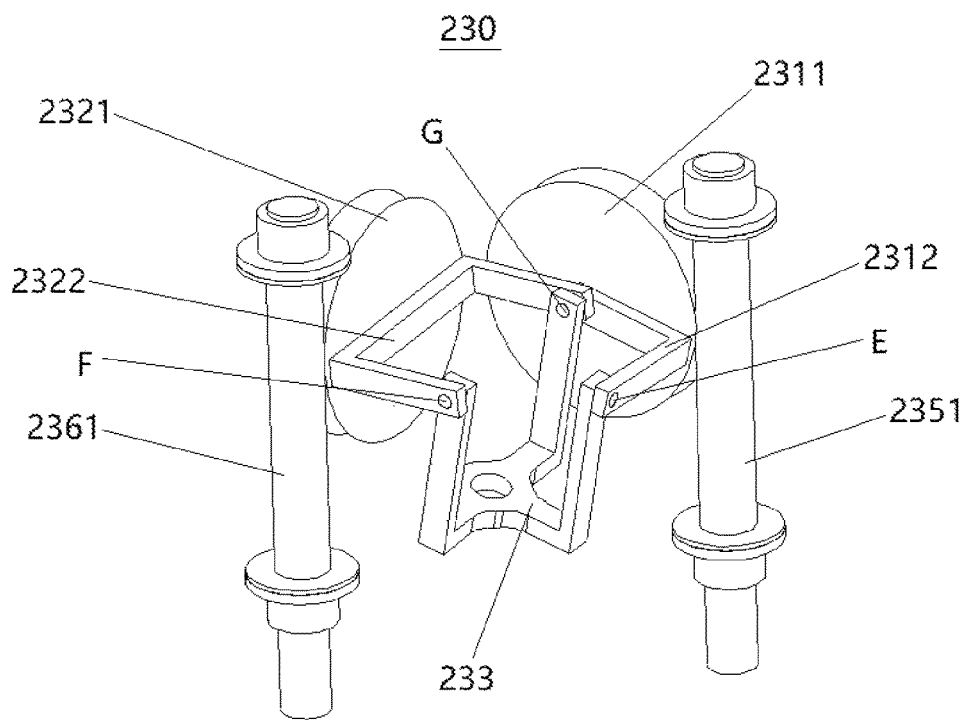
FIG. 15 shows a partial schematic structural diagram of the drive transmission mechanism shown in FIG. 14 according to some embodiments of the present disclosure.

FIGS. 12 and 13 respectively show a partial schematic structural diagram of a continuum instrument 10 (or 20, 30) according to some embodiments of the present disclosure including another drive transmission mechanism 230. FIG. 14 shows a schematic structural diagram of the drive transmission mechanism 230 according to some embodiments of the present disclosure. In some embodiments, as shown in FIGS. 12 and 13, the drive transmission mechanism 230 may include a first rotating member 231, a second rotating member 232, and a driven member 233. The first rotating member 231 is for being driven by a first drive member 235 to rotate, and the second rotating member 232 is driven by the second drive member 236 to rotate. In some embodiments, the axis of rotation of the second rotating member 232 is perpendicular to and intersects the axis of rotation of the first rotating member 231. FIG. 15 shows a partial schematic structural diagram of the drive transmission mechanism 230 according to some embodiments of the present disclosure. As shown in FIGS. 14 and 15, the driven member 233 is separately hinged to the first rotating member 231 and the second rotating member 232 to form a first hinge point E and a second hinge point F, the first rotating member 231 is hinged to the second rotating member 232 to form a third hinge point G, the axis of rotation of the third hinge point G coincides with the axis of rotation of the first rotating member 231, and the driven member 233 is connected to the input end of the drive connection part 120 (or 220). In an initial position, the axis of rotation of the first hinge point E coincides with the axis of rotation of the second rotating member 232, and the axis of rotation of the second hinge point F coincides with the axis of rotation of the first rotating member 231. Thus, the first rotating member 231 and the second rotating member 232 together drive the driven member 233 to rotate around a fixed central point of the drive connection part 120 in the space, the driven member 233 drives the input end of the drive connection part 120 to rotate and thus drive the proximal stop disk 1112 to move and turn so as to achieve the bending of the proximal continuum 111, and then the plurality of proximal structural backbones 1113 which have ends fixed to the proximal stop disk 1112 are pushed and pulled, resulting in the corresponding change in length of the plurality of distal structural backbones 1123 located in the distal continuum 112, so that the distal continuum 112 is driven to bend corresponding to the proximal continuum 111. In this way, the bending of the distal continuum 112 in the space in different directions may be achieved.

In some embodiments, as shown in FIGS. 14 and 15, a first connecting rod member 2312 is fixedly disposed on the first rotating member 231, and a second connecting rod member 2322 is fixedly disposed on the second rotating member 232. One end of the first connecting rod member 2312 is hinged to the driven member 233 to form a first hinge point E, and one end of the second connecting rod member 2322 is hinged to the driven member 233 to form a second hinge point F. The other end of the first connecting rod member 2312 is hinged to the other end of the second connecting rod member 2322 to form a third hinge point G. The third hinge point G is located on the axis of rotation of the first rotating member 231. In some embodiments, the driven member 233 may be hinged to the other end of the first connecting rod member 2312 and the other end of the second connecting rod member 2322 at the third hinge point G. In some embodiments, the driven member 233 may also not be hinged to the other end of the first connecting rod member 2312 and the other end of the second connecting rod member 2322. It should be appreciated that, in the present invention, the first rotating member 231 and the second rotating member 232 may be hinged to the driven member 233 by means of connecting members in other forms other than the first connecting rod member 2312 and the second connecting rod member 2322, as long as the hinge points satisfy the above geometrical relationships.

As shown in FIG. 15, in some embodiments, the first rotating member 231 and the first drive member 235 may respectively include a first worm gear 2311 and a first worm 2351 meshing with each other, the first worm gear 2311 being fixedly connected to the first connecting rod member 2312. The second rotating member 232 and the second drive member 236 may respectively include a second worm gear 2321 and a second worm 2361 meshing with each other, the second worm gear 2321 being fixedly connected to the second connecting rod member 2322. In the drive transmission mechanism 230, by means of providing two worm and gear structures, the direction of rotation of the driven member 233 can be changed, and the amplification of driving torque can be achieved. It will be appreciated that the first rotating member 231 and the second rotating member 232 include, but are not limited to, a worm gear structure, for example, the first rotating member 231 and the second rotating member 232 may also be bevel gears, the first drive member 235 and the second drive member 236 may be driving bevel gears meshing with the bevel gears, the bevel gears are driven by the driving bevel gears to rotate. It should be appreciated that the first rotating member 231 and the second rotating member 232 may also be rotatable members other than gears. In some embodiments, the first drive member 235 and the second drive member 236 may further include an electric motor (a motor), and the first rotating member 231 and the second rotating member 232 may be driven by the electric motor to directly rotate relative to each other.

Figure 16:
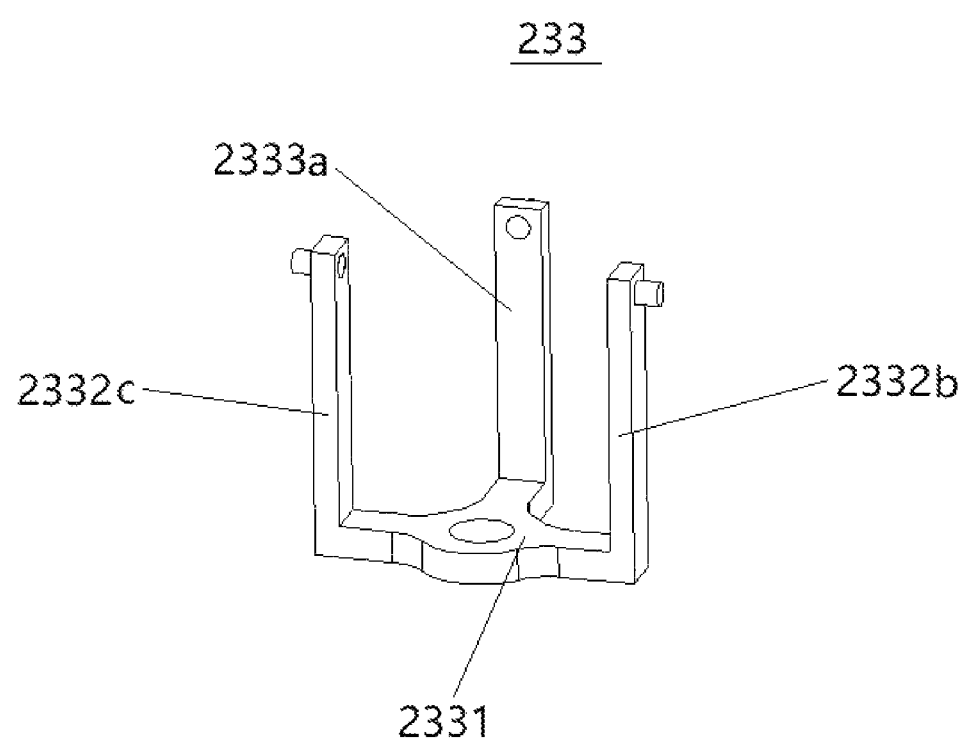
FIG. 16 shows a schematic structural diagram of a driven member of the drive transmission mechanism shown in FIG. 14 according to some embodiments of the present disclosure.

FIG. 16 shows a schematic structural diagram of the driven member 233 of the drive transmission mechanism 230 according to some embodiments of the present disclosure. As shown in FIG. 16, in some embodiments, the driven member 233 may include a connector 2331 connected to the input end of the drive connection part 120 (or 220), and hinged link rods 2332a-b connected to the connector 2331 and extending distally. The hinged link rod 2332a is hinged to one end of the first connecting rod 2312 of the first rotating member 231 at a first hinge point E, and the hinged link rod 2332b is hinged to one end of the second connecting rod 2322 of the second rotating member 232 at the second hinge point F. In some embodiments, as shown in FIG. 16, the driven member 233 may further include a third hinged link rod 2332c connected to the connector 2331 and extending distally. The hinged link rod 2332c is hinged to the other end of the first connecting rod 2312 of the first rotating member 231 and the other end of the second connecting rod 2322 of the second rotating member 232 at the third hinge point G. In some embodiments, the connector 2331 may be integrally formed with or fixedly connected to the hinged link rods 2332a-c.

Thus, as shown in FIGS. 12-14, the first worm gear 2311 and the second worm gear 2321 are respectively driven by the first worm 2351 and the second worm 2361 to drive the first connecting rod 2312 connected to the first worm gear 2311 and the second connecting rod 2322 connected to the second worm gear 2321 to rotate, so as to drive the driven member 233 hinged to the first connecting rod 2312 and the second connecting rod 2322 to rotate around the fixed central point (e.g., a central point of a universal coupling or a central point of a spherical hinge) of the drive connection part 120 (or 220) in the space. The driven member 233 drives the input end of the drive connection part 120 to rotate and thus drive the proximal stop disk 1112 to move and turn, such that the plurality of proximal structural backbones 1113 which have ends fixed to the proximal stop disk 1112 are pushed and pulled to achieve the bending of the proximal continuum 111, and the distal continuum 112 is then driven to bend corresponding to (e.g., in an opposite direction with) the proximal continuum 111 so as to achieve the bending of the distal continuum 112 in the space in different directions. The proportions of bending of the proximal continuum 111 and the distal continuum 112 are respectively inversely proportional to the corresponding distribution radii of the proximal structural backbones 1113 and the distal structural backbones 1123 in the proximal continuum 111 and the distal continuum 112 (in this embodiment, the proximal structural backbones 1113 and the distal structural backbones 1123 in the proximal continuum 111 and the distal continuum 112 are distributed in a circumferential direction, may be distributed on a circumference or in a peripheral direction of a rectangular, polygonal, elliptical or other shape, and may be in a uniform or non-uniform distribution, which will not be limited herein). When in use, the distribution radii of the proximal structural backbones 1113 and the distal structural backbones 1123 in the proximal continuum and the distal continuum may be respectively adjusted to meet the actual requirements of the proportion of bending. The proximal structural backbones can be pushed and pulled by means of driving the proximal stop disk to turn, which prevents the proximal structural backbones from being directly pushed and pulled, such that a large number of proximal structural backbones can be driven without being limited by the number of drive transmission mechanisms, achieving a compact structure and very high reliability and flexibility.

In some embodiments, as shown in FIG. 5, the following connection nodes of kinematic relationship may be included among the drive connection part 320 (or 120, 220), the proximal continuum 111, and the drive transmission mechanism 130 (or 230): a first connection node A which may refer to the connection relationship between the proximal base disk 1111 and the drive connection part 320 (or 120, 220), a second connection node B which may refer to the structure of the drive connection part itself (e.g., a universal coupling, a spherical hinge or a hinge joint), a third connection node C which may refer to the connection relationship between the drive connection part 320 and the proximal stop disk 1112, and a fourth connection node D which may refer to the connection relationship between the input end of the drive connection part 320 and the drive transmission mechanism 130. The above four connection nodes may be combined in some of the following connection modes: a cylindrical pair (which may be rotatable or movable), a moving pair, a rotating pair (which can rotate only), a fixed connection, and the structure of the drive connection part itself, so as to achieve the minimum degree of freedom required for driving the proximal continuum 111 to bend by means of combining the above connection nodes.

In some embodiments, as shown in FIG. 7, when the drive transmission mechanism uses a gear-barrel-based non-planar drive transmission mechanism 130, the input end of the drive connection part 120 (or 220, 320) is rotatably connected to the drive transmission mechanism 130 in a vertical direction of the axial direction of the proximal end of the drive connection part 120, and the input end of the drive connection part 120 is rotatably connected in the axial direction of the proximal end of the drive connection part 120 relative to the proximal stop disk 1112. In some embodiments, when the drive transmission mechanism uses the gear-barrel-based non-planar drive transmission mechanism 130, the distal end of the drive connection part 120 (or 220, 320) is connected to the proximal base disk 1111 by means of a rotating pair in the axial direction of the distal end of the drive connection part 120, or the proximal end of the drive connection part 120 is connected to the proximal stop disk 1112 by means of a rotating pair in the axial direction of the proximal end of the drive connection part 120, and the input end of the drive connection part 120 is rotatably connected to the drive transmission mechanism 130 in the vertical direction of the axial direction of the rotating pair in the axial direction of the proximal end of the drive connection part 120.

As shown in FIGS. 2(a), 2(b) and 7, in some embodiments, the drive transmission mechanism uses a gear-barrel-based non-planar drive transmission mechanism 130, and the drive connection part 120 may include the universal coupling joint 121. The connection nodes may be combined as follows. The first connection node A is connected by using a rotating pair, the second connection node B is connected by using a universal coupling 1211, the third connection node C is connected by using a cylindrical pair, the fourth connection node D is connected by using a rotating pair, and the axis of rotation of the fourth connection node D is perpendicular to the axial direction of the proximal end of the drive connection part 120. For example, the universal coupling joint 121 includes the link rods 1212a-b and the universal coupling 1211 located between the link rods 1212a-b. The first connection node A may refer to the structure in which the distal end of the link rod 1212a at the distal end of the universal coupling 1211 is connected to the proximal base disk 1111 by means of the rotating pair, the second connection node B may refer to the structure of the universal coupling 1211 itself, the proximal end of the link rod 1212b at the proximal end of the universal coupling 1211 is the input end of the drive connection part 120, the third connection node C may refer to the structure in which an outer circular surface of the link rod 1212b cooperates with the proximal stop disk 1112 by means of the cylindrical pair, the fourth connection node D may refer to the structure in which the input end of the link rod 1212b is connected to the arc-shaped link rod 1341 in the drive transmission mechanism 130 by means of the rotating pair, and the axis of rotation of the rotating pair connection is perpendicular to the axial direction of the link rod 1212b. Therefore, the proximal stop disk 1112 is slidable and rotatable relative to the outer circular surface of the input end. The input end is driven to rotate by means of the arc-shaped link rod 1341 of the drive transmission mechanism 130, so that the proximal stop disk 1112 may be driven to cooperatively turn so as to achieve the bending of the proximal continuum 111, and a plurality of proximal structural backbones 1113 which have ends fixed to the proximal stop disk 1112 are then pushed and pulled, so as to drive the distal continuum 112 to bend corresponding to (e.g., in an opposite direction with) the proximal continuum 111. Thus, the above four connection nodes cooperate with each other such that the proximal stop disk 1112 can slip or rotate up and down relative to the drive connection part 120, or the drive connection part 120 can slide or rotate up and down relative to the arc-shaped link rod 1341, so as to allow the proximal continuum 111 to generate a parasitic motion sliding in the axial direction (slipping up and down) and a bending motion in any direction (rotation) during bending. The parasitic motion may prevent the distal continuum 112 from generating an axial telescoping motion during bending that may cause wrinkling or excessive stretching of an envelope that covers the outer periphery of the distal continuum 112 to affect the service life of the cover.

As shown in FIG. 7, in some embodiments, the drive transmission mechanism uses the gear-barrel-based non-planar drive transmission mechanism 130, the drive connection part 120 may include the universal coupling joint 121, and the connection nodes may also be combined as follows: the first connection node A is connected by using a rotating pair, the second connection node B is connected by using the universal coupling 1211, the third connection node C is connected by using a rotating pair, the fourth connection node D is connected by using a rotating pair, and the axis of rotation of the fourth connection node D is perpendicular to the axial direction of the proximal end of the drive connection part 120. In this way, it is also possible to enable the input end to be driven by the arc-shaped link rod 1341 to rotate and thus drive the proximal stop disk 1112 to move and turn so as to achieve the bending of the distal continuum 112. In some embodiments, the connection nodes may also be combined as follows: the first connection node A is connected by using a cylindrical pair, the second connection node B is connected by using the universal coupling 1211, the third connection node C is connected by using a moving pair, the fourth connection node D is connected by using a rotating pair, and the axis of rotation of the fourth connection node D is perpendicular to the axial direction of the proximal end of the drive connection part 120. It should be appreciated that the connection nodes may also be combined in other forms of some of the above five connection modes, such that under the premise of achieving a similar function (driving the proximal continuum 111 to bend), the more degrees of freedom, the more pliable and flexible the flexible continuum structure 110 will be.

Figure 4A:
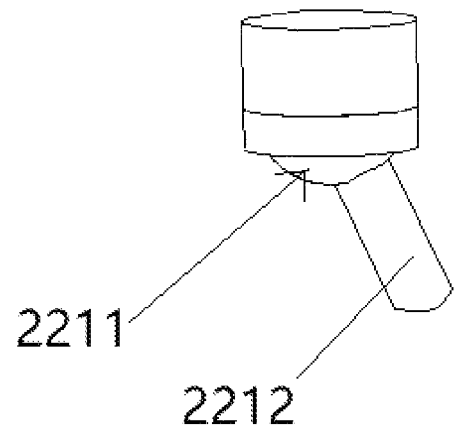
FIG. 4(a) shows a schematic structural diagram of a spherical hinge joint of a drive connection part according to some embodiments of the present disclosure.
Figure 4B:
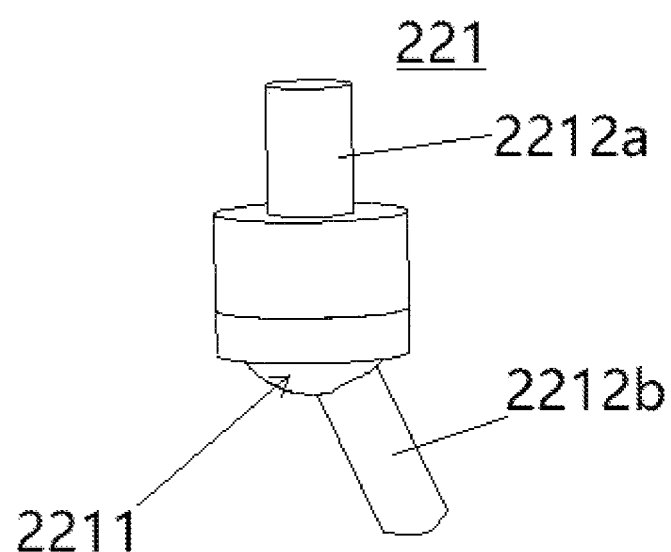
FIG. 4(b) shows a schematic structural diagram of another spherical hinge joint of the drive connection part according to some embodiments of the present disclosure.

As shown in FIGS. 4(a), 4(b) and 7, in some embodiments, the drive transmission mechanism uses a gear-barrel-based non-planar drive transmission mechanism 130, and the drive connection part 220 may include the spherical hinge joint 221. In this way, the connection nodes may be combined as follows: the first connection node A is connected in a fixed manner, the second connection node B is connected by using the spherical hinge 2211, the third connection node C is connected by using a cylindrical pair, the fourth connection node D is connected by using a rotating pair, and the axis of rotation of the fourth connection node D is perpendicular to the axial direction of the proximal end of the drive connection part 220. For example, the drive connection part 220 includes the link rods 2212a-b and the spherical hinge 2211 located between the link rods 2212a-b. The first connection node A may refer to the structure in which a distal end of the link rod 2212a at a distal end of the spherical hinge 2211 is connected to the proximal base disk 1111 by means of the rotating pair, the second connection node B may refer to the structure of the spherical hinge itself, a proximal end of the link rod 2212b at a proximal end of the spherical hinge 2211 is the input end of the drive connection part 220, the third connection node C may refer to the structure in which an outer circular surface of the link rod 2212b cooperates with the proximal stop disk 1112 by means of the cylindrical pair, the fourth connection node D may refer to the structure in which the input end of the link rod 2212b is connected to the arc-shaped link rod 1341 in the drive transmission mechanism 130 by means of the rotating pair, and the axis of rotation of the rotating pair connected is perpendicular to the axial direction of the link rod 2212b. Therefore, the proximal stop disk 1112 is slidable and rotatable relative to the outer circular surface of the input end. In this way, the input end is driven to rotate by means of the arc-shaped link rod 1341 of the drive transmission mechanism 130, so that the proximal stop disk 1112 may be driven to cooperatively turn so as to achieve the bending of the proximal continuum 111, and a plurality of proximal structural backbones 1113 which have ends fixed to the proximal stop disk 1112 are then pushed and pulled, so as to drive the distal continuum 112 to bend corresponding to (e.g., in an opposite direction with) the proximal continuum 111.

In some embodiments, the drive transmission mechanism uses the gear-barrel-based non-planar drive transmission mechanism 130, and the connection nodes may also be combined as follows: the first connection node A is connected by using a cylindrical pair, the second connection node B is connected by using the spherical hinge 2211, the third connection node C is connected in a rotatable manner, and the fourth connection node D is connected by using a rotating pair.

As shown in FIGS. 6 and 7, in some embodiments, the drive transmission mechanism uses the gear-barrel-based non-planar drive transmission mechanism 130, and the hinge joint of the drive connection part 320 may include the distal link rod 3211 and the proximal link rod 3212. The connection nodes may be combined as follows: the first connection node A uses a rotating pair, the second connection node B uses a rotating pair, the third connection node C uses a cylindrical pair, and the fourth connection node D uses a rotating pair. For example, the first connection node A may refer to the structure in which the distal end of the distal link rod 3211 is rotatable around its own axis in the proximal base disk 1111; the second connection node B may refer to the structure in which the proximal end of the distal link rod 3211 is hinged to the distal end of the proximal link rod 3212, the structure of the drive connection part 320 itself is configured as the distal link rod 3211 and the proximal link rod 3212 hinged to each other, and the proximal end of the proximal link rod 3212 serves as the input end of the drive connection part 320; the third connection node C refers to the structure in which an outer peripheral surface of the proximal link rod 3212 cooperates with the proximal stop disk 1112 by means of a cylindrical pair, and the proximal stop disk 1112 is slidable and rotatable relative to the input end of the proximal link rod 3212; and the fourth connection node D refers to the structure in which the input end of the proximal link rod 3212 is hinged to the drive transmission mechanism 130, and the axis of rotation of a hinge point is perpendicular to the axial direction of the proximal end of the drive connection part 320. The input end of the proximal link rod 3212 is driven to rotate by means of the drive transmission mechanism 130, the proximal stop disk 1112 is driven to cooperatively turn so as to achieve the bending of the proximal continuum 111, and a plurality of proximal structural backbones 1113 which have ends fixed to the proximal stop disk 1112 are then pushed and pulled so as to drive the distal continuum 112 to bend corresponding to (e.g., in an opposite direction with) the proximal continuum 111.

In some embodiments, the drive transmission mechanism uses the gear-barrel-based non-planar drive transmission mechanism 130, and the connection nodes may also be combined as follows: the first connection node A uses a cylindrical pair, the second connection node B uses a rotating pair, the third connection node C uses a rotating pair, the fourth connection node D uses a rotating pair, and the axis of rotation of the fourth connection node D is perpendicular to the axial direction of the proximal end of the drive connection part 320. In this way, it is also possible to allow the input end of the drive connection part 320 to be driven by the drive transmission mechanism 130 to move in a free rotational motion and thus drive the proximal stop disk 1112 to move and turn so as to achieve the bending of the distal continuum 112.

As shown in FIG. 12, in some embodiments, when the drive transmission mechanism uses a worm-and-gear-based non-planar drive transmission mechanism 230, the input end of the drive connection part 120 (or 220) and the drive transmission mechanism 230 may be fixedly connected or connected by using a rotating pair or a cylindrical pair, etc.

As shown in FIGS. 2(a), 2(b) and 12, in some embodiments, the drive transmission mechanism uses the worm-and-gear-based non-planar drive transmission mechanism 230, and the drive connection part 120 may include the universal coupling joint 121. The connection nodes may be combined as follows: the first connection node A is connected by using a cylindrical pair, the second connection node B is connected by using the universal coupling 1211, the third connection node C has a degree of freedom of movement (a cylindrical pair or a moving pair), and the fourth connection node D is connected in a fixed manner. For example, the universal coupling joint 121 includes the link rods 1212a-b and the universal coupling 1211 located between the link rods 1212a-b. The first connection node A may refer to the structure in which the distal end of the link rod 1212a at the distal end of the universal coupling 1211 cooperates with the proximal base disk 1111 by means of the cylindrical pair, the second connection node B may refer to the structure of the universal coupling 1211 itself, the proximal end of the link rod 1212b at the proximal end of the universal coupling 1211 is the input end of the drive connection part 120, the third connection node C may refer to the structure in which the outer circular surface of the link rod 1212b cooperates with the proximal stop disk 1112 by means of the cylindrical pair (or the moving pair), and the fourth connection node D may refer to the structure in which the input end of the link rod 1212b is fixedly connected to the driven member 233. Therefore, the proximal stop disk 1112 is slidable and rotatable relative to the input end. The fixed central point of the drive connection part 120 is the center of the universal coupling 1211, the driven member 233 rotates around the center of the universal coupling 1211, the input end is thus driven by the driven member 233 to move in a rotational motion to drive the proximal stop disk 1112 to cooperatively turn, and a plurality of proximal structural backbones 1113 which have ends fixed to the proximal stop disk 1112 are then pushed and pulled so as to achieve the bending of the proximal continuum 111 and thus drive the distal continuum 112 to bend corresponding to (e.g., in an opposite direction with) the proximal continuum 111. The above nodes cooperate with each other such that the proximal stop disk 1112 can slip or rotate up and down relative to the drive connection part 120 or the drive connection part 120 can slip or rotate up and down relative to the driven member 233, so as to allow the proximal continuum 111 to generate a parasitic motion sliding in the axial direction (slipping up and down) and a bending motion in any direction (rotation) during bending.

In some embodiments, the drive transmission mechanism uses the worm-and-gear-based non-planar drive transmission mechanism 230, and the drive connection part 120 may include the universal coupling joint 121. The connection nodes may also be combined as follows: the first connection node A is connected by using a rotating pair, the second connection node B is connected by the universal coupling 1211, the third connection node C is connected by using a rotating pair, and the fourth connection node D is connected by using a rotating pair. It is also possible to allow the input end of the drive connection part 120 to be driven by the drive transmission mechanism 230 to rotate and thus drive the proximal stop disk 1112 to move and turn so as to achieve the bending of the distal continuum 112. In some embodiments, the nodes may also be combined as follows: the first connection node A is connected in a fixed manner, the second connection node B uses the universal coupling 1211, the third connection node C is connected in a fixed manner, and the fourth connection node D is connected by using a moving pair. It should be appreciated that the above connection nodes may also be combined in other forms of some of the above five connection modes, such that under the premise of achieving a similar function (driving the proximal continuum 111 to bend), the more degrees of freedom, the more pliable and flexible the flexible continuum structure 110 will be.

As shown in FIGS. 4(a), 4(b) and 12, in some embodiments, the drive transmission mechanism uses the worm-and-gear-based non-planar drive transmission mechanism 230, and the drive connection part 220 may include the spherical hinge joint 221. The connection nodes may be combined as follows: the first connection node A is connected in a fixed manner, the second connection node B is connected by using the spherical hinge 2211, the third connection node C is connected by using a cylindrical pair, and the fourth connection node D is connected in a fixed manner. For example, the drive connection part 220 includes the link rods 2212a-b and the spherical hinge 2211 located between the link rods 2212a-b. The first connection node A may refer to the structure in which a distal end of the link rod 2212a at a distal end of the spherical hinge 2211 is fixedly connected to the proximal base disk 1111, the second connection node B may refer to the structure of the spherical hinge joint 221 itself, a proximal end of the link rod 2212b at a proximal end of the spherical hinge 2211 is the input end of the drive connection part 220, the third connection node C may refer to the structure in which the outer circular surface of the link rod 2212b cooperates with the proximal stop disk 1112 by means of the cylindrical pair, and the fourth connection node D may refer to the structure in which the input end of the link rod 2212b is fixedly connected to the driven member 233. Therefore, the proximal stop disk 1112 is slidable and rotatable relative to the input end. The fixed central point of the drive connection part 220 is the center of the spherical hinge 2211, the driven member 233 rotates around the center of the spherical hinge 2211, the input end is thus driven by the driven member 233 to move a rotational motion to drive the proximal stop disk 1112 to cooperatively turn, and a plurality of proximal structural backbones 1113 which have ends fixed to the proximal stop disk 1112 are then pushed and pulled so as to achieve the bending of the proximal continuum 111 and thus drive the distal continuum 112 to bend corresponding to (e.g., in an opposite direction with) the proximal continuum 111. The above connection nodes cooperate with each other such that the proximal stop disk 1112 can slip or rotate up and down relative to the drive connection part 220 or the drive connection part 220 can slip or rotate up and down relative to the driven member 233, so as to allow the proximal continuum 111 to generate a parasitic motion sliding in the axial direction (slipping up and down) and a bending motion in any direction (rotation) during bending.

In some embodiments, the drive transmission mechanism uses the worm-and-gear-based non-planar drive transmission mechanism 230, and the drive connection part 220 may include the spherical hinge joint 221. The connection nodes may also be combined as follows: the first connection node A is connected by using a rotating pair, the second connection node B is connected by using the spherical hinge 2211, the third connection node C is connected by using a moving pair, and the fourth connection node D is connected in a fixed manner. In this way, it is also possible to allow the driven member 233 to be driven by the drive transmission mechanism 230 to rotate to drive the input end to rotate and thus drive the proximal stop disk 1112 to move and turn so as to achieve the bending of the distal continuum 112. In some embodiments, the connection nodes may also be combined as follows: the first connection node A is connected in a fixed manner, the second connection node B uses the spherical hinge 2211, the third connection node C is connected in a rotatable manner, and the fourth connection node D is connected by using a moving pair.

As shown in FIG. 1, in some embodiments, the proximal continuum 111 may further include at least one proximal retaining disk 1114 disposed between the proximal base disk 1111 and the proximal stop disk 1112, and the plurality of proximal structural backbones 1113 sequentially pass through the at least one proximal retaining disk 1114. As shown in FIG. 1, in some embodiments, the distal continuum 112 may further include at least one distal retaining disk 1124 disposed between the distal base disk 1121 and the distal stop disk 1122, and the plurality of distal structural backbones 1123 may also sequentially pass through the at least one distal retaining disk 1124. The proximal retaining disk 1114 and the distal retaining disk 1124 are for respectively supporting the structural backbones in the radial directions of the proximal structural backbones 1113 and the distal structural backbones 1123, so that the proximal structural backbones 1113 and the distal structural backbones 1123 remain in a parallel state during the bending transformation, which can prevent the proximal structural backbones 1113 and the distal structural backbones 1123 from destabilizing during the bending motion. In some embodiments, at least one tube bundle retaining disk 1131 (see FIG. 17) is disposed on the structural backbone guide tube bundle 113, a proximal end of the structural backbone guide tube bundle 113 is fixedly connected to the proximal base disk 1111, and a distal end of the structural backbone guide tube bundle 113 passes through the at least one tube bundle retaining disk 1131 and is then fixedly connected to the distal base disk 1121.

In some embodiments, the proximal structural backbone 1113 and the distal structural backbone 1123 may include elastic wires or tubes made of a hyperelastic material, for example, may be made of an elastic metallic material having high strength and high toughness, such as a nickel-titanium alloy. The structural backbone guide tube bundle 113 may include a plurality of thin tubes made of a steel material to form a steel tube bundle.

In some embodiments, the continuum instrument 40 may include at least two continuum instruments 10 (or 20, 30) in the embodiments described above. In some embodiments, the continuum instrument 40 includes at least two continuum instruments 10 (or 20, 30) connected in series or in parallel.

Figure 17:
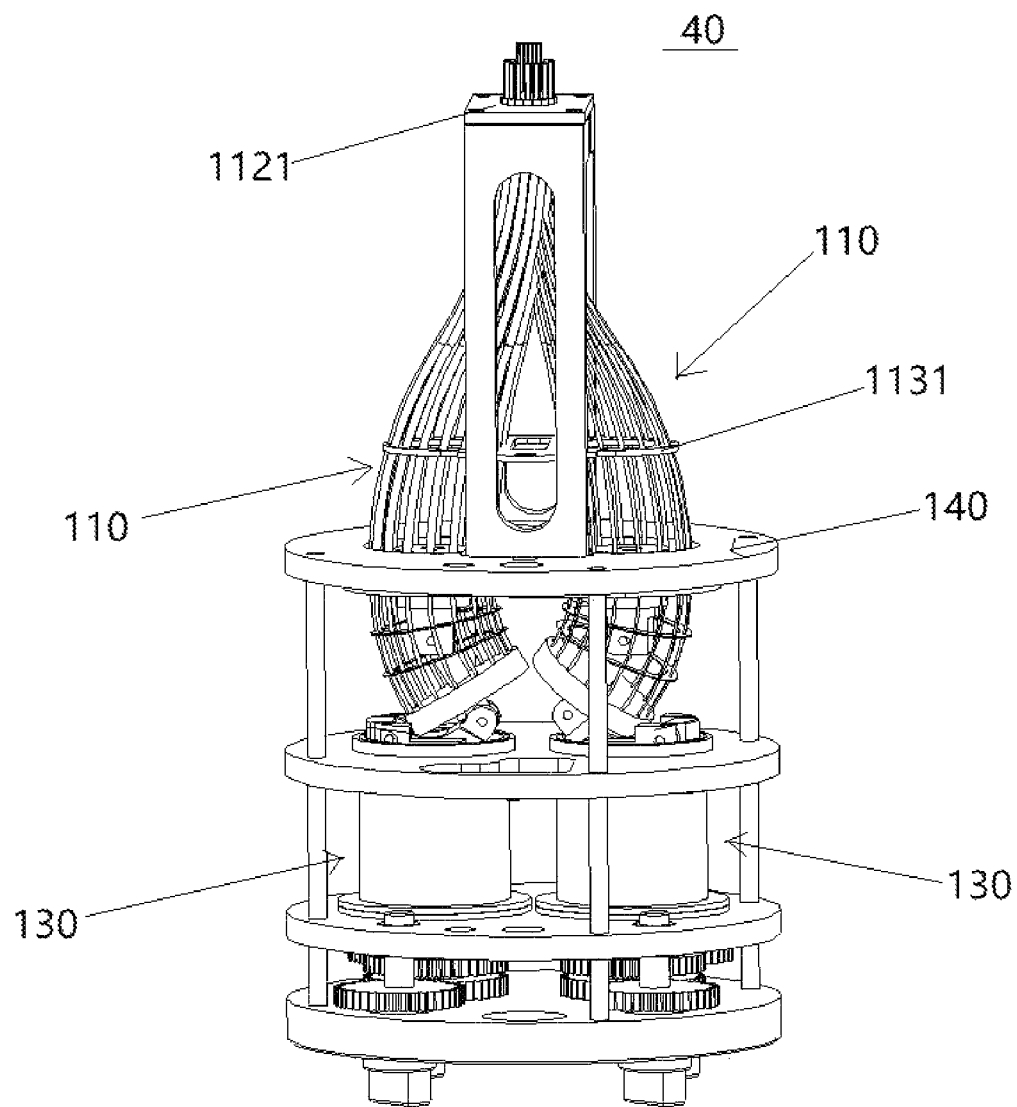
FIG. 17 shows a partial schematic structural diagram of another continuum instrument according to some embodiments of the present disclosure.
Figure 18:
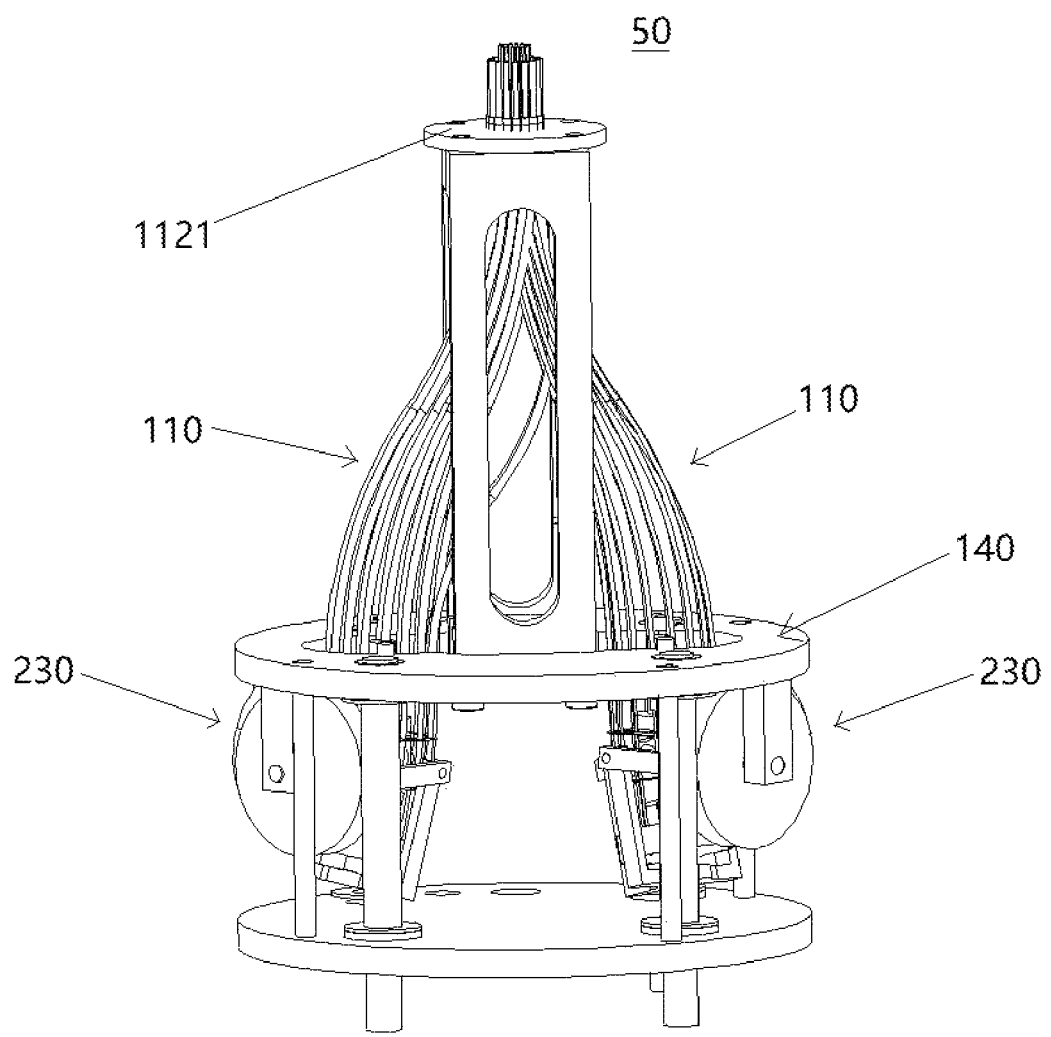
FIG. 18 shows a partial schematic structural diagram of another continuum instrument according to some embodiments of the present disclosure.

FIGS. 17 and 18 respectively show partial schematic structural diagrams of the continuum instrument 40 and a continuum instrument 50 according to some embodiments of the present disclosure. As shown in FIG. 17, in some embodiments, the continuum instrument 40 (or the continuum instrument 50) further includes a support 140. The proximal base disks 1111 of the at least two flexible continuum structures 110 are respectively fixedly connected to or integrally formed with the support 140, the proximal ends of the at least two structural backbone guide tube bundles 113 are respectively fixedly connected to the proximal base disks 1111 of the proximal continua 111, and the distal ends of the at least two structural backbone guide tube bundles 113 respectively pass through the support 140 in sequence and converge into one bundle at the distal base disk 1121, for example, the distal ends of the two structural backbone guide tube bundles 113 are distributed at the distal base disk 1121 along the circumference as one bundle or distributed within the circle. It should be appreciated that the distal ends of the two structural backbone guide tube bundles 113 may also be distributed at the distal base disk 1121 along the rectangular periphery as one bundle or distributed within the rectangle. In some embodiments, the proximal base disk 1111 or the distal base disk 1121 may directly form part of the support 140. In some embodiments, as shown in FIG. 17, at least two drive transmission mechanisms 130 are arranged side by side on the support 140, with an output end of each drive transmission mechanism 130 being connected to the input end of at least one drive connection part 120 (or 220, 320). The at least two drive transmission mechanisms 130 respectively drive the proximal stop disks 1112 of the at least two flexible continuum structures 110 by means of the at least two input ends to move and turn, so that the proximal structural backbones 1113 of the at least two flexible continuum structures 110 are pushed and pulled so as to achieve the bending of at least two distal continua 112 in a space in different directions. In some embodiments, as shown in FIG. 18, at least two drive transmission mechanisms 230 are arranged side by side on the support 140, the output end of each drive transmission mechanism 230 is separately connected to the input ends of at least two drive connection parts 120 (or 220), and the proximal stop disks 1112 of the two flexible continuum structures 110 are respectively driven by the at least two input ends to move and turn, so that the proximal structural backbones 1113 of the at least two flexible continuum structures 110 are pushed and pulled so as to achieve the bending of at least two distal continua 112 in the space in different directions.

In some embodiments, the distal continua 112 in the at least two flexible continuum structures 110 of the continuum instrument 40 (or the continuum instrument 50) may have the same or different lengths. It will be appreciated that the distal ends of at least two structural backbone guide tube bundles 113 are converged at the distal base disk 1121. At least two distal continua 112 may be connected in series. For example, the proximal end of the first distal continuum distally extends from the distal base disk 1121 and is fixedly connected to the distal stop disk 1122, the distal base disk of the second distal continuum is connected to or is the same as the distal stop disk 1122 of the first distal continuum, and the distal end of the second distal continuum may be fixedly connected to the distal stop disk 1122. Thus, the at least two drive transmission mechanisms 130 (or 230) respectively drive the at least two drive connection parts 120 (or 220) to move to respectively drive the at least two proximal continua 111 to move, so that the distal continua 112 bends so as to increase the degree of freedom of the distal continua 112 and thus improve the flexibility of the continuum instrument.

Figure 19:
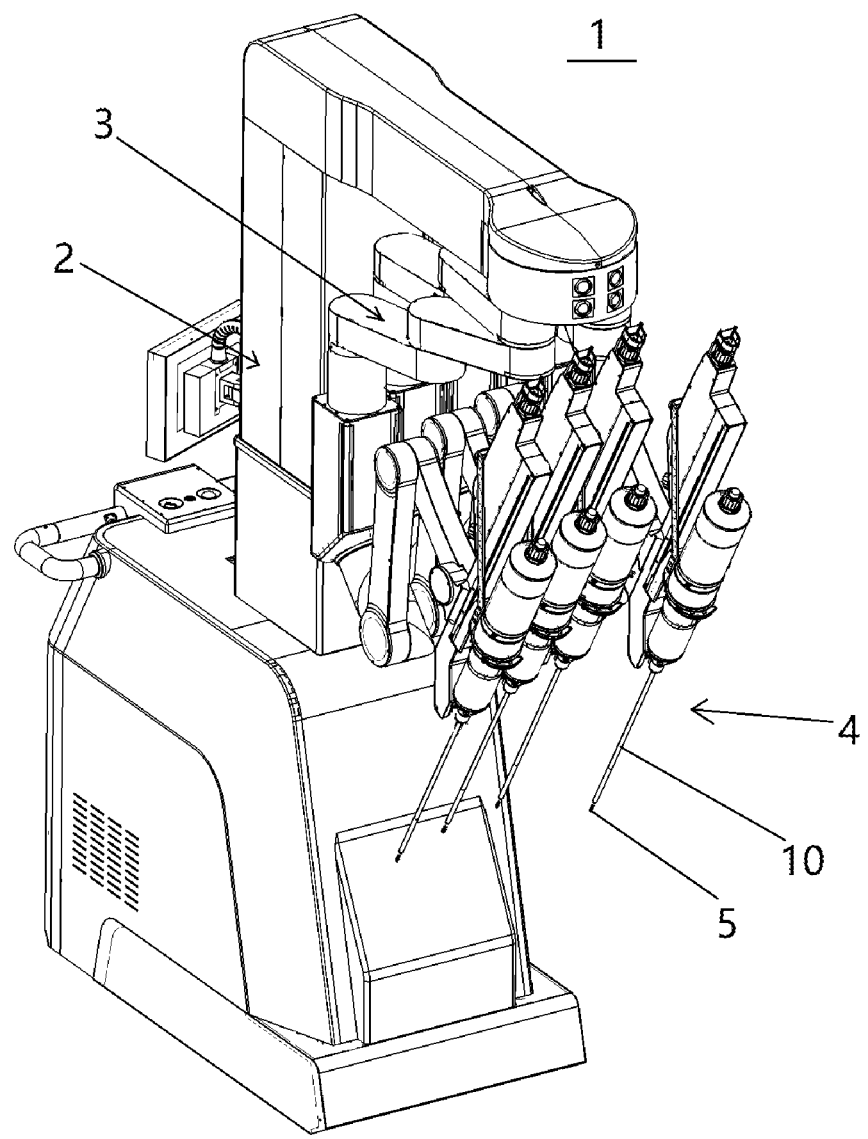
FIG. 19 shows a schematic structural diagram of a surgical robot according to some embodiments of the present disclosure.

In some embodiments, the present disclosure further provides a surgical robot. The surgical robot includes at least one continuum instrument 10 (or 20, 30, 40, 50) in the embodiments described above. FIG. 19 shows a schematic structural diagram of a surgical robot 1 according to some embodiments of the present disclosure. As shown in FIG. 19, in some embodiments, the surgical robot 1 may further include at least one surgical trolley 2, at least one positioning arm 3, and at least one surgical instrument 4. At least one positioning arm 3 is movably disposed on the at least one surgical trolley 2, and at least one surgical instrument 4 is disposed at the distal end of the at least one positioning arm 3. The surgical instrument 4 includes the continuum instrument 10 (or the continuum instruments 20, 30, 40, 50) and an end device 5 disposed at the distal end of the continuum instrument 10. It should be appreciated that the end device 5 may include a surgical end effector or an endoscope. The position of the continuum instrument may be adjusted by means of adjusting the positioning arm 3, and the posture of the end device 5 may be adjusted by means of the continuum instrument. The continuum instrument is compact in structure and has high reliability and flexibility, and can improve the safety of the surgical robot.

It should be noted that the foregoing description merely includes exemplary embodiments of the present disclosure and the technical principles applied. It will be appreciated by those skilled in the art that the present disclosure is not limited to the particular embodiments herein, and various obvious changes, readjustments and substitutions can be made by those skilled in the art without departing from the scope of protection of the present disclosure. Therefore, although the present disclosure has been described in detail with reference to the above embodiments, the present disclosure is not limited merely to the above embodiments, and can also include more other equivalent embodiments without departing from the concept of the present disclosure, and the scope of protection of the present disclosure is determined by the scope of the appended claims.

The invention claimed is:

1. A continuum instrument, comprising:
   at least one proximal continuum comprising a proximal stop disk and a plurality of proximal structural backbones, proximal ends of the plurality of proximal structural backbones being fixedly connected to the proximal stop disk;
   at least one distal continuum comprising a distal stop disk and a plurality of distal structural backbones, distal ends of the plurality of distal structural backbones being fixedly connected to the distal stop disk, and the plurality of distal structural backbones being fixedly connected to or integrally formed with the plurality of proximal structural backbones; and
   a drive connection part connected to the proximal stop disk and comprising an input end located at a proximal side of the proximal stop disk, the input end being used for driving the proximal stop disk to turn so as to drive the distal continuum to bend by means of the proximal structural backbones and the distal structural backbones,
   wherein the proximal continuum further comprises a proximal base disk through which the plurality of proximal structural backbones pass, a distal end of the drive connection part is connected to the proximal base disk, and a proximal end of the drive connection part passes through the proximal stop disk; and
   wherein the proximal stop disk is connected to the proximal base disk via the drive connection part by means of at least two rotating pairs which have axes intersecting each other, and the drive connection part comprises at least one rotating pair having a radial axis.

2. The continuum instrument according to claim 1, wherein a connection between the drive connection part and the proximal stop disk or a connection between the drive connection part and the proximal base disk includes at least one of a cylindrical pair, a moving pair, a rotating pair, or a fixed connection.

3. The continuum instrument according to claim 1, wherein the drive connection part comprises at least one universal coupling joint which comprises a universal coupling and at least one link rod, the at least one universal coupling joint has a distal end connected to the proximal base disk and a proximal end passing through and connected to the proximal stop disk, and the at least one universal coupling joint comprises the input end located at the proximal side of the proximal stop disk; or
   the drive connection part comprises at least one spherical hinge joint which comprises a spherical hinge and at least one link rod, the at least one spherical hinge joint has a distal end connected to the proximal base disk and a proximal end passing through and connected to the proximal stop disk, and the at least one spherical hinge joint comprises the input end located at the proximal side of the proximal stop disk; or the drive connection part comprises at least one hinge joint, which comprises:
a distal link rod, which has a distal end connected to the proximal base disk; and
a proximal link rod, which has a distal end hinged to the distal link rod, with a hinge axis being perpendicular to axial directions of the distal link rod and the proximal link rod, and has a proximal end penetrating the proximal stop disk and connected to the proximal stop disk, the proximal link rod comprising the input end located at the proximal side of the proximal stop disk.

4. The continuum instrument according to claim 1, further comprising: a drive transmission mechanism, an output end of the drive transmission mechanism being connected to the input end of the drive connection part and outputting a non-planar motion.

5. The continuum instrument according to claim 4, wherein the drive transmission mechanism comprises:
a first rotatable member configured to be driven by a first drive member to rotate;
a second rotatable member coaxially disposed with the first rotatable member and configured to be driven by a second drive member to rotate relative to the first rotatable member;
a rotary-linear motion mechanism connected to the first rotatable member and configured to convert a rotational motion of the first rotatable member into a linear motion to be output; and
a connecting member, which has one end hinged to the output end of the rotary-linear motion mechanism and the other end hinged to the input end of the drive connection part.

6. The continuum instrument according to claim 5, wherein the rotary-linear motion mechanism comprises:
a guide member having a proximal end fixedly connected to the second rotatable member;
a rotary member having a proximal end passing through the second rotatable member and being fixedly connected to the first rotatable member; and
a moving member rotatably connected to the rotary member and for being guided by the guide member to move linearly in an axial direction of the guide member.

7. The continuum instrument according to claim 6, wherein the drive transmission mechanism further comprises a barrel-shaped member sleeved outside the moving member, a proximal end of the barrel-shaped member being fixedly connected to the second rotatable member; and
the proximal end of the guide member is fixedly connected to the second rotatable member, a distal end of the guide member is fixedly connected to the barrel-shaped member, and the moving member is slidably disposed on the guide member in a penetrating manner.

8. The continuum instrument according to claim 6, wherein the drive transmission mechanism further comprises a barrel-shaped member sleeved outside the moving member, a proximal end of the barrel-shaped member being fixedly connected to the second rotatable member; and
the guide member comprises a guide rod and a guide groove cooperating with each other, the guide groove being fixedly disposed on the barrel-shaped member in an axial direction of the barrel-shaped member, the guide rod being slidably disposed in the guide groove, and the guide rod being fixedly connected to the moving member.

9. The continuum instrument according to claim 6, wherein the rotary member comprises a lead screw, and the moving member comprises a nut and a sliding block, the nut being rotatably connected to the lead screw.

10. The continuum instrument according to claim 9, wherein the connecting member comprises an arc-shaped link rod, and the sliding block comprises an upper-layer hinge portion and a lower-layer cylindrical portion which are fixedly connected to each other or integrally formed with each other, the upper-layer hinge portion is hinged to one end of the arc-shaped link rod, and the lower-layer cylindrical portion is fixedly sleeved outside the nut.

11. The continuum instrument according to claim 4, wherein the drive transmission mechanism comprises:
a first rotating member configured to be driven by the first drive member to rotate;
a second rotating member configured to be driven by the second drive member to rotate, an axis of rotation of the second rotating member being perpendicular to and intersecting an axis of rotation of the first rotating member; and
a driven member hinged to the first rotating member at a first hinge point and hinged to the second rotating member at a second hinge point, the first rotating member being hinged to the second rotating member at a third hinge point, an axis of rotation of the third hinge point coinciding with an axis of rotation of the first rotating member, and the driven member being connected to the input end of the drive connection part; and
in an initial position, an axis of rotation of the first hinge point coinciding with an axis of rotation of the second rotating member, and an axis of rotation of the second hinge point coinciding with an axis of rotation of the first rotating member.

12. The continuum instrument according to claim 11, wherein a first connecting rod member is fixedly disposed on the first rotating member, and a second connecting rod member is fixedly disposed on the second rotating member; and
one end of the first connecting rod member is hinged to the driven member at the first hinge point, one end of the second connecting rod member is hinged to the driven member at the second hinge point, and the other end of the first connecting rod member is hinged to the other end of the second connecting rod member at the third hinge point.

13. The continuum instrument according to claim 12, wherein the driven member is hinged to the first rotating member and the second rotating member at the third hinge point.

14. The continuum instrument according to claim 12, wherein the driven member comprises a connector connected to the input end of the drive connection part, and at least two connecting rods connected to the connector and extending distally, one of the connecting rods being hinged to the first rotating member, and the other of the connecting rods being hinged to the second rotating member.

15. The continuum instrument according to claim 1, wherein the distal continuum further comprises a distal base disk through which the plurality of distal structural backbones pass; the continuum instrument further comprises at least one structural backbone guide tube bundle connected between the proximal base disk and the distal base disk; and the plurality of proximal structural backbones pass through the proximal base disk and the at least one structural backbone guide tube bundle, and are fixedly connected to or integrally formed with the plurality of distal structural backbones.

16. The continuum instrument according to claim 15, comprising:
at least two proximal continua, at least two distal continua, at least two structural backbone guide tube bundles, at least two drive connection parts, and at least two drive transmission mechanisms,
the at least two proximal continua are connected in series or in parallel.

17. The continuum instrument according to claim 16, further comprising: a support, wherein
the proximal base disks of the at least two proximal continua are respectively fixedly connected to or integrally formed with the support, the proximal ends of the at least two structural backbone guide tube bundles are respectively fixedly connected to the proximal base disks of the proximal continua, and the distal ends of the at least two structural backbone guide tube bundles pass through the support and converge into one bundle at the same distal base disk; and
the at least two drive transmission mechanisms are arranged side by side on the support, and the output end of each of the drive transmission mechanisms is connected to the input end of corresponding drive connection part to drive the proximal stop disk of the corresponding proximal continuum to turn, so as to drive corresponding distal continuum to bend.

18. A surgical robot comprising:
at least one surgical trolley;
at least one positioning arm movably disposed on the at least one surgical trolley; and
at least one surgical instrument disposed at a distal end of the at least one positioning arm;
wherein the at least one surgical instrument comprises at least one continuum instrument and an end device disposed at a distal end of the continuum instrument;
wherein the continuum instrument comprises:
at least one proximal continuum comprising a proximal stop disk and a plurality of proximal structural backbones, proximal ends of the plurality of proximal structural backbones being fixedly connected to the proximal stop disk;
at least one distal continuum comprising a distal stop disk and a plurality of distal structural backbones, distal ends of the plurality of distal structural backbones being fixedly connected to the distal stop disk, and the plurality of distal structural backbones being fixedly connected to or integrally formed with the plurality of proximal structural backbones; and
a drive connection part connected to the proximal stop disk and comprising an input end located at a proximal side of the proximal stop disk, the input end being used for driving the proximal stop disk to turn so as to drive the distal continuum to bend by means of the proximal structural backbones and the distal structural backbones; and
the proximal continuum further comprises a proximal base disk through which the plurality of proximal structural backbones pass, a distal end of the drive connection part is connected to the proximal base disk, and a proximal end of the drive connection part passes through the proximal stop disk; and
wherein the proximal stop disk is connected to the proximal base disk via the drive connection part by means of at least two rotating pairs which have axes intersecting each other, and the drive connection part comprises at least one rotating pair having a radial axis.

* * * * *